United States Patent [19]
Bock et al.

[11] Patent Number: 5,175,159
[45] Date of Patent: Dec. 29, 1992

[54] 3-SUBSTITUTED-1,4-BENZODIAZEPINES AS OXYTOCIN ANTAGONISTS

[75] Inventors: Mark G. Bock, Hatfield; Ben E. Evans, Lansdale; Roger M. Freidinger, Lansdale, all of Pa.

[73] Assignee: Merck & Co., Inc., Rahway, N.J.

[21] Appl. No.: 633,168

[22] Filed: Dec. 28, 1990

Related U.S. Application Data

[63] Continuation of Ser. No. 417,412, Oct. 5, 1989, abandoned.

[51] Int. Cl.⁵ .................. A61K 31/55; C07D 243/24; C07D 243/16; C07D 243/14
[52] U.S. Cl. ...................... 514/221; 540/504; 540/505; 540/506; 540/507; 540/508; 540/509; 540/510; 540/512; 540/514; 540/569; 540/570; 540/571; 540/573
[58] Field of Search .............. 540/504, 505, 506, 507, 540/508, 509, 510, 512, 514, 569, 570, 571, 573; 514/221

[56] References Cited

U.S. PATENT DOCUMENTS 4,628,084 12/1986 Bock et al. .................. 540/509
4,820,834 4/1989 Evans et al. .................. 540/504

OTHER PUBLICATIONS

Journal of Medicinal Chemistry, 32, 1 (1989), Bock, et al.

Primary Examiner—Robert T. Bond
Attorney, Agent, or Firm—Frank P. Grassler; Joseph F. DiPrima

[57] ABSTRACT

Compounds of Formula I are antagonists of oxytocin and are useful in the treatment of preterm labor and dysmenorrhea, and for stoppage of labor prepatory to Caesarean delivery.

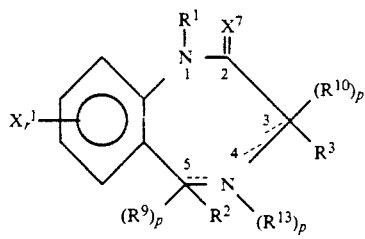

7 Claims, No Drawings

3-SUBSTITUTED-1,4-BENZODIAZEPINES AS OXYTOCIN ANTAGONISTS

This is a continuation of application Ser. No. 07/417,412, filed on Oct. 5, 1989, now abandoned.

BACKGROUND OF THE INVENTION

This invention pertains to the field of obstetrics.

In this field, one of the most important problems is the management of preterm labor. A significant number of the pregnancies progressing past 20 weeks of gestation experience premature labor and delivery which is a leading cause of neonatal morbidity and mortality.

It has recently been proposed that a selective oxytocin antagonist would be the ideal tocolytic agent. In the last few years, evidence has accumulated to suggest strongly that oxytocin is the physiological initiator of labor in several mammalian species including humans. Oxytocin is believed to exert this effect in part by directly contracting the uterine myometrium and in part by enhancing the synthesis and release of contractile prostaglandins from the uterine endometrium/decidua. These prostaglandins may, in addition, be important in the cervical ripening process. By these mechanisms, the process of labor (term and preterm) is initiated by a heightened sensitivity of the uterus to oxytocin, resulting in part by a well-documented increase in the number of oxytocin receptors in this tissue. This 'up-regulation' of oxytocin receptors and enhanced uterine sensitivity appears to be due to trophic effects of rising plasma levels of estrogen towards term. By blocking both the direct (contractile) and indirect (enhanced prostaglandin synthesis) effects of oxytocin on the uterus, a selective oxytocin antagonist would likely be more efficacious for treating preterm labor than current regimens. In addition, since oxytocin at term has major effects only on the uterus, such a compound would be expected to have few, if any, side effects.

The compounds of the present invention may also be useful for the treatment of dysmenorrhea. This condition is characterized by cyclic pain associated with menses during ovulatory cycles. The pain is thought to result from uterine contractions and ischemia, probably mediated by the effect of prostaglandins produced in the secretory endometrium. By blocking both the direct and indirect effects of oxytocin on the uterus, a selective oxytocin antagonist may be more efficacious for treating dysmenorrhea than current regimens.

An additional use for the present invention is for the stoppage of the labor prepatory to Caesarean delivery.

It was, therefore, a purpose of this invention to identify substances which more effectively antagonize the function of oxytocin in disease states in animals, preferably mammals, especially in humans. It was another purpose of this invention to prepare novel compounds which more selectively inhibit oxytocin. It was still another purpose of this invention to develop a method of antagonizing the functions of oxytocin in disease states in mammals. It is also a purpose of this invention to develop a method of preventing or treating oxytocin related disorders, particularly preterm labor and dysmenorrhea.

SUMMARY OF THE INVENTION

It has now been found that compounds of Formula I are antagonists of oxytocin and bind to the oxytocin receptor. These compounds are useful in the treatment and prevention of oxytocin-related disorders of animals, preferably mammals and especially humans. These disorders are primarily preterm labor and dysmenorrhea. The compounds would also find usefulness for stoppage of labor preparatory to Caesarian delivery.

DETAILED DESCRIPTION OF THE INVENTION

Within the invention are the novel compounds of Formula I:

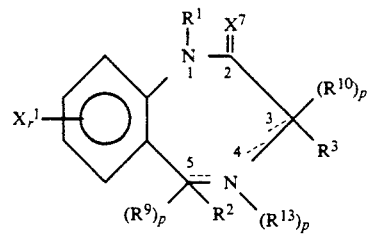

wherein
$R^1$ is H, $C_1$–$C_6$ linear or branched alkyl, loweralkenyl, lower alkynyl, —$X^{12}COOR^6$, —$X^{11}$-cycloloweralkyl, —$X^{12}NR^4R^5$, —$X^{12}CONR^4R^5$, —$X^{12}CN$, or —$X^{11}CX_3^{10}$;

$R^2$ is H, loweralkyl, substituted or unsubstituted phenyl (wherein the substitutents may be 1 or 2 of halo, loweralkyl, loweralkoxy, loweralkylthio, carboxyl, carboxyloweralkyl, nitro, —$CF_3$, or hydroxy), 2-, 3-, 4-pyridyl,

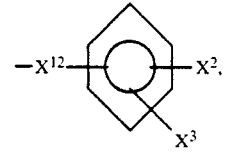

—$X^{12}SCH_3$, —$x^{12}SOCH_3$, —$X^{12}SO_2CH_3$, or —$X^{12}COOR^6$;

$R^3$ is H, —$X^{11}NR^{18}Xa^{11}R^7$,

—$NHX^{11}NHR^7$, —$NHX^{11}NHCOR^7$,

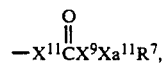

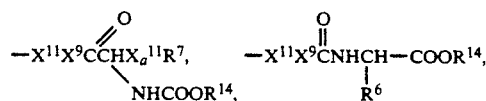

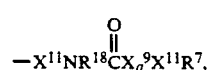

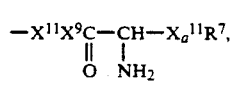

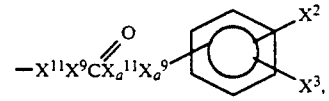

-continued

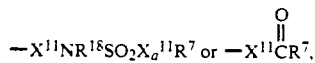

R$^4$ and R$^5$ are independently R$^6$ or in combination with the N of the NR$^4$R$^5$ group form an unsubstituted or mono or disubstituted, saturated or unsaturated, 4-7 membered heterocyclic ring, or benzofused 4-7 membered heterocyclic ring, or said heterocyclic ring or said benzofused heterocylic ring which further comprises a second heteroatom selected from O and NCH$_3$ and the substituent(s) is/are independently selected from C$_{1-4}$alkyl;

R$^6$ is H, loweralkyl, cycloloweralkyl, substituted or unsubstituted phenyl, or substituted or unsubstituted phenylloweralkyl wherein the phenyl or phenylloweralkyl substituents may be 1 or 2 of halo, loweralkyl, loweralkoxy, nitro, or CF$_3$;

R$^7$ is loweralkyl, cycloloweralkyl, X$^{12}$-cycloloweralkyl, wherein cycloloweralkyl encompasses C$_3$-C$_{20}$ and may be mono or polycyclic, including bridged, fused ring and spiro units, and such cycloloweralkyl units may be unsubstituted or independently substituted at one or two of the secondary carbons with the following substituents:

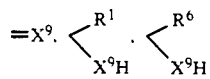

R$^9$ and R$^{10}$ are independently H, —OH, or —CH$_3$;
R$^{13}$ is H, loweralkyl, acyl, O, cycloloweralkyl,

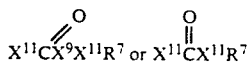

R$^{14}$ is loweralkyl or phenylloweralkyl;
R$^{15}$ is H, loweralkyl,

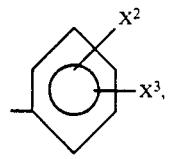

or —NH$_2$;
R$^{18}$ is H, OH, OR$^{13}$, or loweralkyl;
p is 0 when its adjacent ⎓ is unsaturated and 1 when its adjacent ⎓ is saturated except that when R$^{13}$ is O, p=1 and ⎓ is unsaturated;
r is 1 or 2;
X$^1$ is H, —NO$_2$, CF$_3$ CN, OH, loweralkyl, halo, loweralkylthio, loweralkoxy, —X$^{11}$COOR$^6$, or —X$^{11}$NR$^4$R$^5$;
X$^2$ and X$^3$ are independently H, —OH, —NO$_2$, halo, loweralkylthio, loweralkyl, or loweralkoxy;
X$^7$ is O, S, HH, or NR$^{15}$ with the proviso that X$^7$ can be NR$^{15}$ only when R$^1$ is not H;
X$^9$ and X$_a^9$ are independently NR$^{18}$ or O;
X$^{10}$ is F, Cl, or Br;
X$^{11}$ and X$_a^{11}$ are independently absent or C$_{1-4}$ linear or branched alkyl;
X$^{12}$ is C$_{1-4}$ linear or branched alkyl;
⎓ is a saturated or unsaturated bond;

and the pharmaceutically acceptable salts thereof, with the proviso that R$^3$ is H when and only when R$^{13}$ is

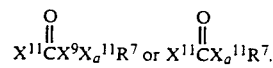

Preferred compounds of Formula I are those wherein
R$^1$ is H, C$_1$-C$_6$ linear or branched alkyl;
R$^2$ is substituted or unsubstituted phenyl (wherein the substitutents may be 1 or 2 of halo, loweralkyl, loweralkoxy, loweralkylthio, carboxyl, carboxyloweralkyl, nitro, —CF$_3$, or hydroxy);
R$^3$ is —X$^{11}$NR$^{18}$X$_a^{11}$R$^7$,

—NHX$^{11}$NHR$^7$, —NHX$^{11}$NHCOR$^7$,

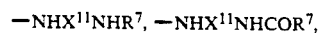

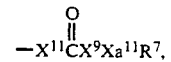

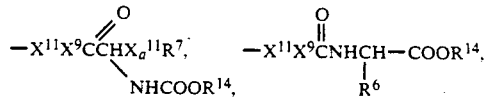

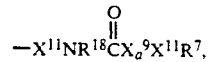

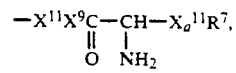

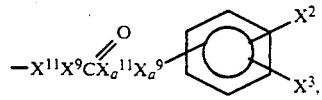

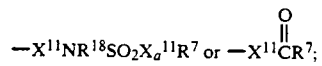

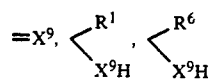

R$^6$ is H, loweralkyl, cycloloweralkyl, substituted or unsubstituted phenyl, or substituted or unsubstituted phenylloweralkyl wherein the phenyl or phenylloweralkyl substituents may be 1 or 2 of halo, loweralkyl, loweralkoxy, nitro, or CF$_3$;

R$^7$ is loweralkyl, cycloloweralkyl, X$^{12}$-cycloloweralkyl, wherein cycloloweralkyl encompasses C$_3$-C$_{20}$ and may be mono or polycyclic, including bridged, fused ring and spiro units, and such cycloloweralkyl units may be unsubstituted or independently substituted at one or two of the secondary carbons with the following substituents:

=X$^9$, $\begin{matrix} R^1 \\ X^9H \end{matrix}$, $\begin{matrix} R^6 \\ X^9H \end{matrix}$ R$^9$ and R$^{10}$ are independently H;
R$^{13}$ is H;
R$^{14}$ is loweralkyl or phenylloweralkyl;
R$^{15}$ is H, loweralkyl,

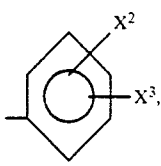

or —NH$_2$;

R$^{18}$ is H, OH, or loweralkyl;

p is 0 when its adjacent ⎓ is unsaturated and 1 when its adjacent ⎓ is saturated;

r is 1;

X$^1$ is H;

X$^7$ is O;

X$^9$ and X$_a^9$ are independently NR$^{18}$ or O;

X$^{11}$ and X$_a^{11}$ are independently absent or C$_{1-4}$ linear or branched alkyl;

X$^{12}$ is C$_{1-4}$ linear or branched alkyl

⎓ is a saturated or unsaturated bond;

and the pharmaceutically acceptable salts thereof.

As used herein, the definition of each expression, e.g. a, p, r, loweralkyl, etc., when it occurs more than once in any structure, is intended to be independent of its definition elsewhere in the same structure. Thus, the ring fragment

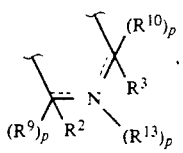

since each p is independently 1 or 0, represents the three structures

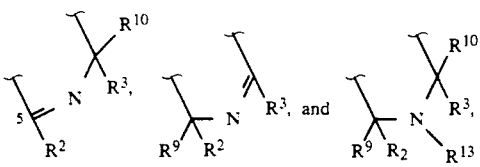

when R$^{13}$ is not O.

As used herein, halo is F, Cl, Br or I; loweralkyl is 1-7 carbon straight or branched chain alkyl and includes methyl, ethyl, propyl, isopropyl, butyl, isobutyl, and t-butyl, pentyl, hexyl, and heptyl; in loweralkoxy and loweralkylthio, the alkyl portion is loweralkyl as previously defined; cycloloweralkyl is cycloalkyl of 3-20 carbons and may be mono or polycyclic as, for example, in cyclohexyl, bicyclo[2,2,2]-octyl, or 1- or 2-adamantyl, loweralkenyl is 1-5 carbon straight or branched chain alkenyl; acyl is formyl, acetyl, propionyl, benzoyl or butyryl; loweralkynyl is 1-5 carbon straight or branched chain alkynyl.

The pharmaceutically acceptable salts of the compounds of Formulas I include the conventional non-toxic salts or the quarternary ammonium salts of the compounds of Formula I formed, e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of Formula I which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The pharmaceutically acceptable salts of the acids of Formula I are also readily prepared by conventional procedures such as treating an acid of Formula I with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quarternary ammonium hydroxide such as tetramethylammonium hydroxide and the like.

An embodiment of this invention is the preparation of compounds of Formula I.

The ability of the compounds of Formula I to antagonize oxytocin makes these compounds useful as pharmaceutical agents for mammals, especially for humans, for the treatment and prevention of disorders wherein oxytocin may be involved. Examples of such disorders include preterm labor and especially dysmenorrhea. These compounds may also find usefulness for stoppage of labor prepatory to Caesarian delivery. Because of the known relationships of vasopressin to oxytocin, the compounds of the present invention are also useful vasopressin antagonists. They are useful in the treatment or prevention of disease states involving vasopressin disorders.

The compounds of Formula I may be administered to a human subject either alone or, preferably, in combination with pharmaceutically-acceptable carriers or diluents, optionally with known adjuvants, such as alum, in a pharmaceutical composition, according to standard pharmaceutical practice. The compounds can be administered orally or parenterally, including intravenous, intramuscular, intraperitoneal and subcutaneous.

For oral use of an antagonist of oxytocin according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

When a compound according to Formula I is used as an antagonist of oxytocin in a human subject, the daily dosage will normally be determined by the prescribing physician with the dosage generally varying according to the age, weight, and response of the individual patient, as well as the severity of the patient's symptoms. However, in most instances, an effective daily dosage will be in the range of from about 0.2 mg/kg to about 10 mg/kg of body weight administered in single or divided doses. In some cases, however, it may be necessary to use dosages outside these limits.

The compounds of Formula I are prepared according to the following schemes.

REACTION SCHEME I

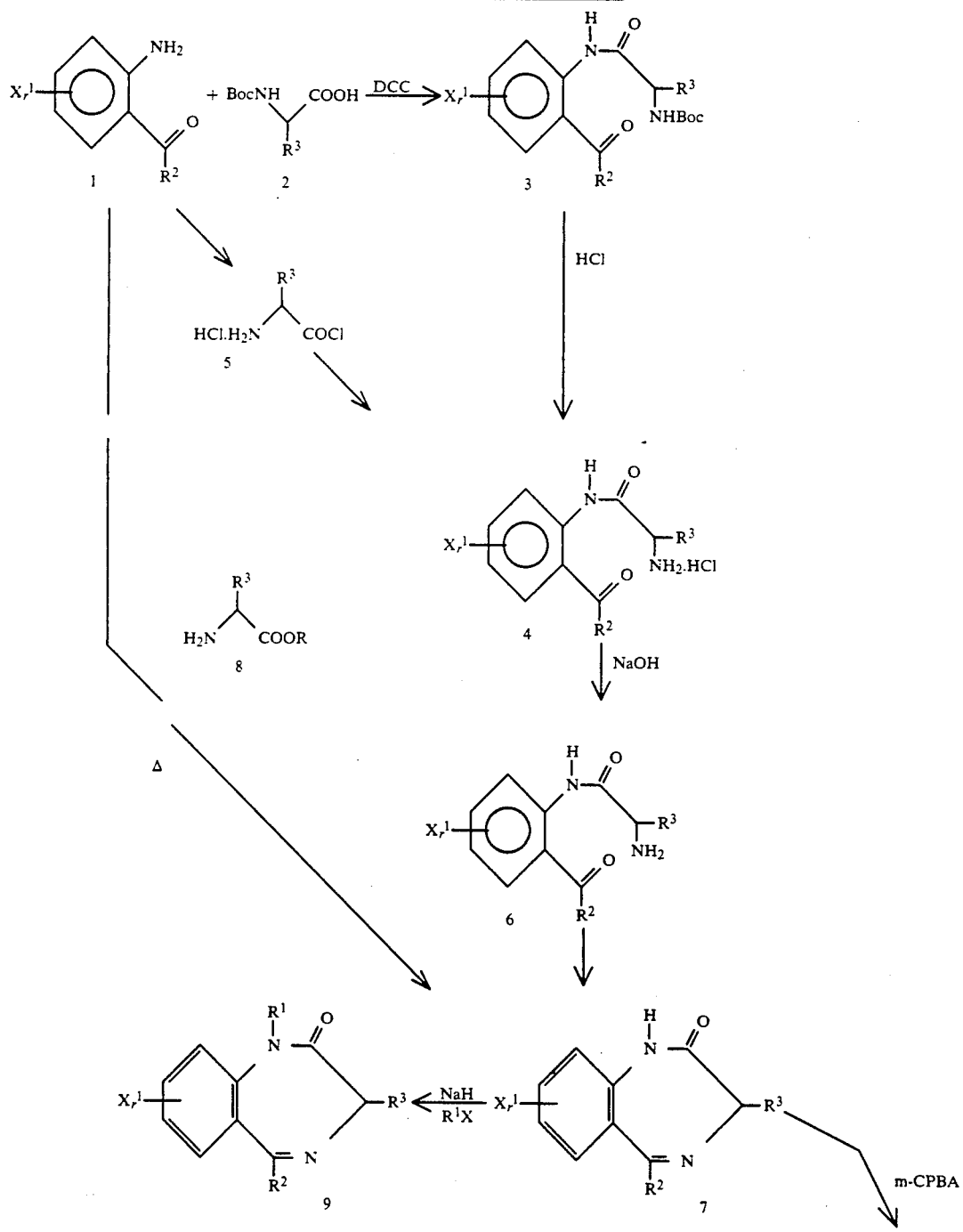

REACTION SCHEME I
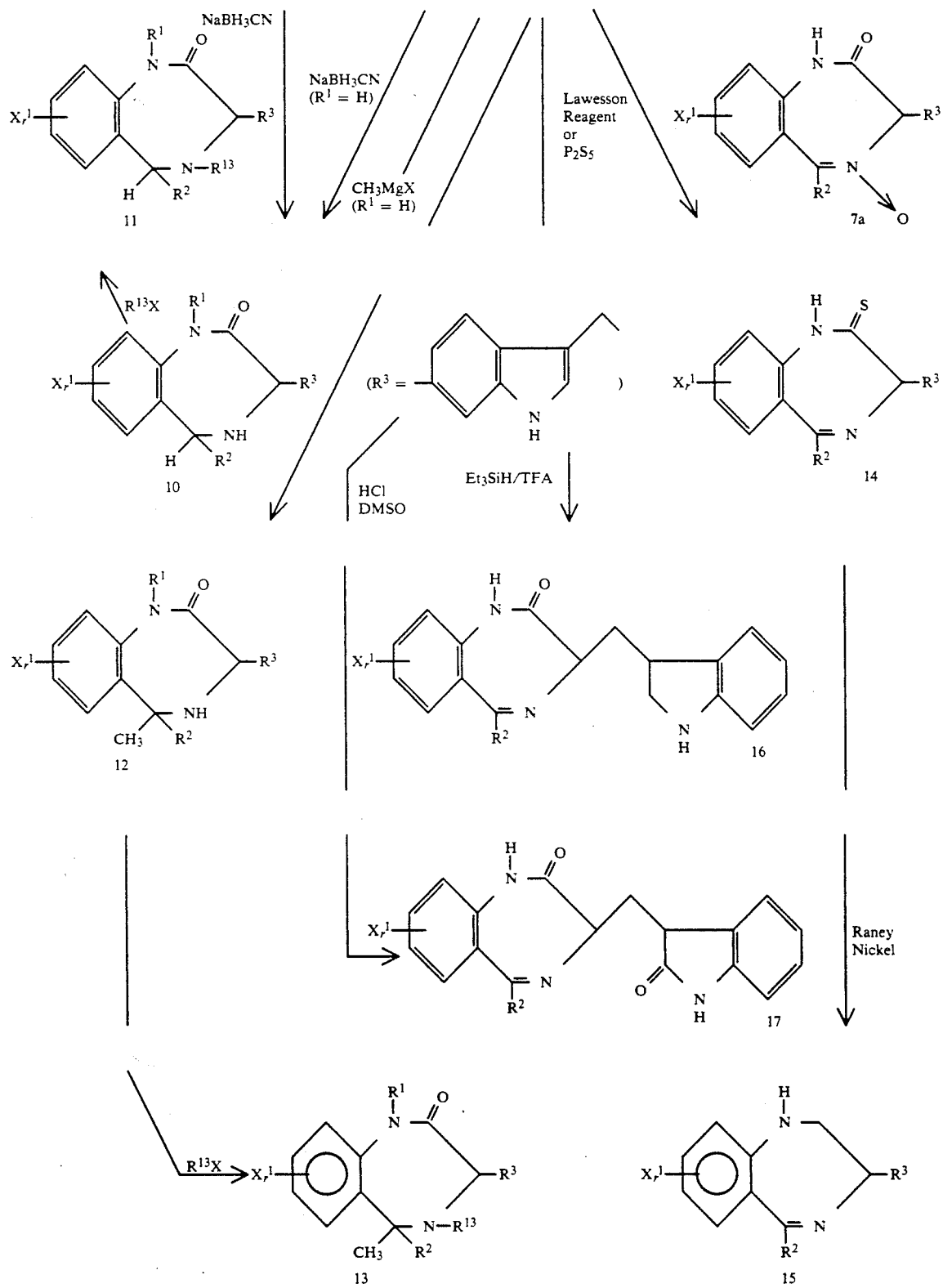

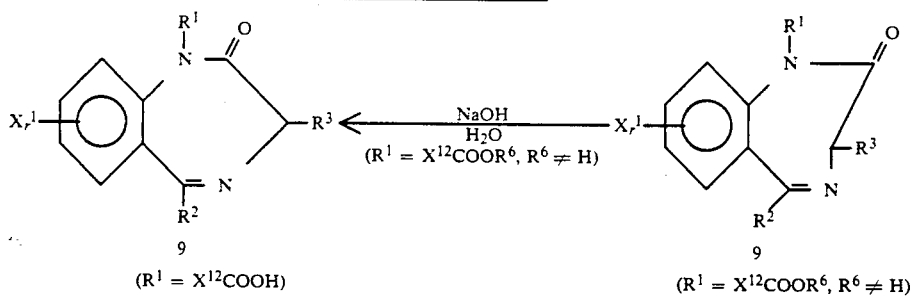
-continued
REACTION SCHEME I
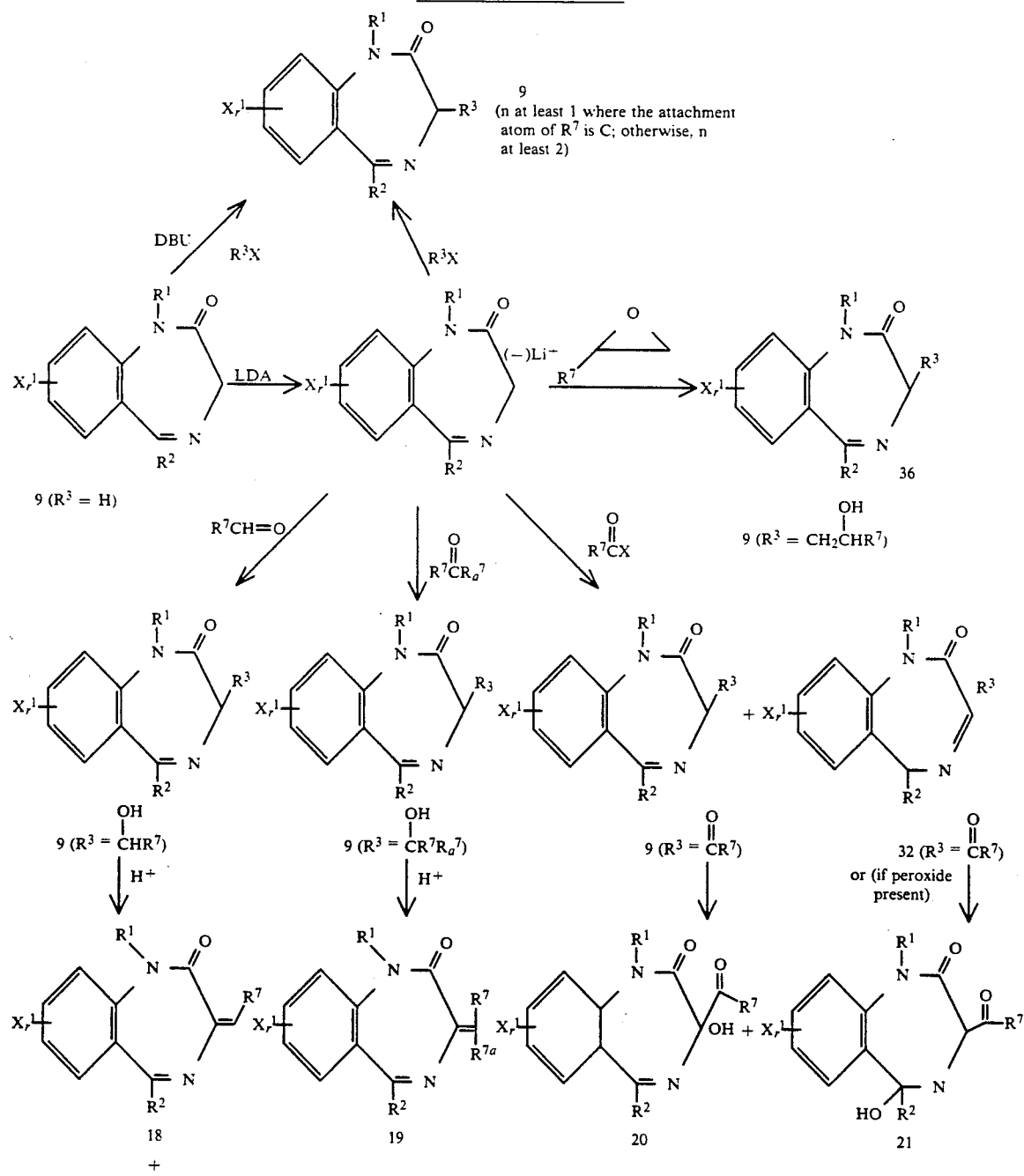
REACTION SCHEME II

-continued
REACTION SCHEME II
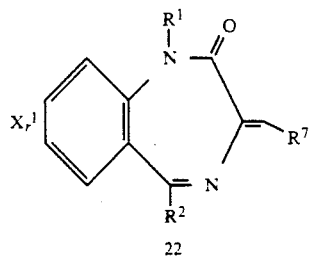
REACTION SCHEME III
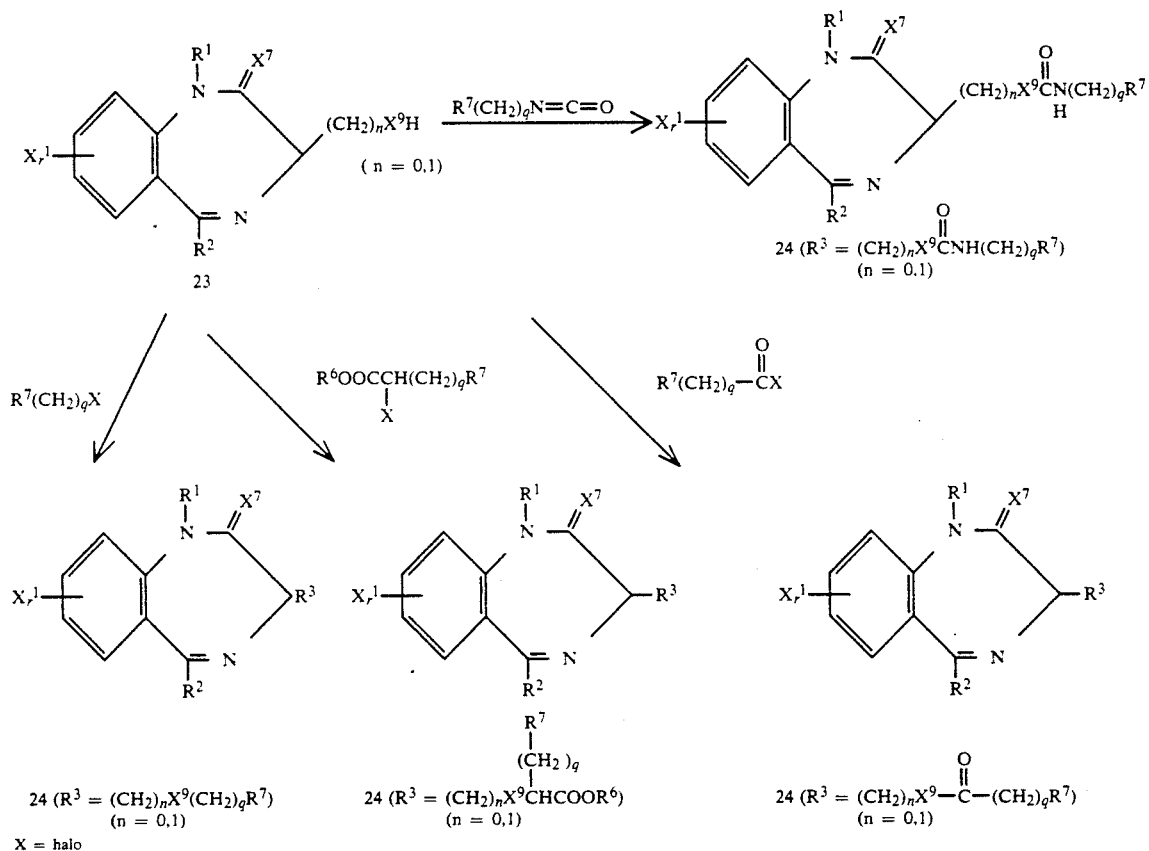
REACTION SCHEME IIIa
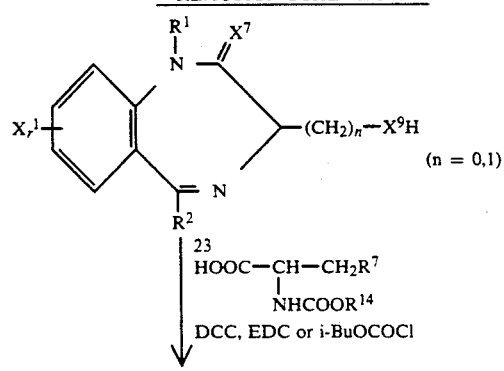
-continued
REACTION SCHEME IIIa
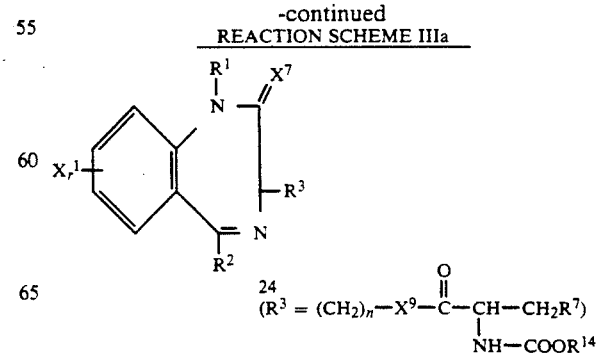

REACTION SCHEME IIIb
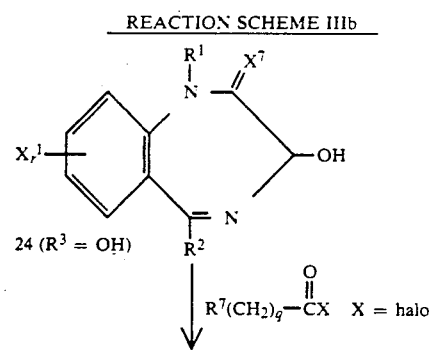
24 (R³ = OH)
R⁷(CH₂)_q—CX   X = halo
-continued
REACTION SCHEME IIIb
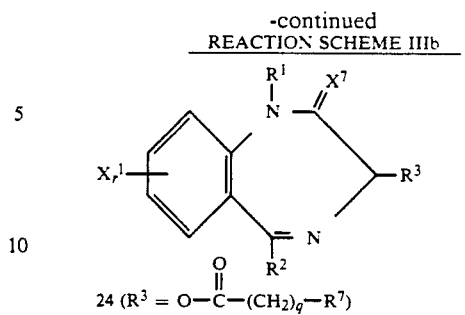
24 (R³ = O—C(=O)—(CH₂)_q—R⁷)
REACTION SCHEME IIIc
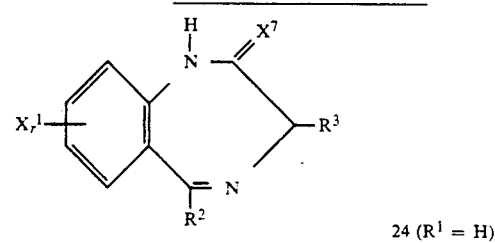
24 (R¹ = H)
NaH, CH₂=CHZ (Z = CN, COOMe, COOEt)      NaH, R¹X
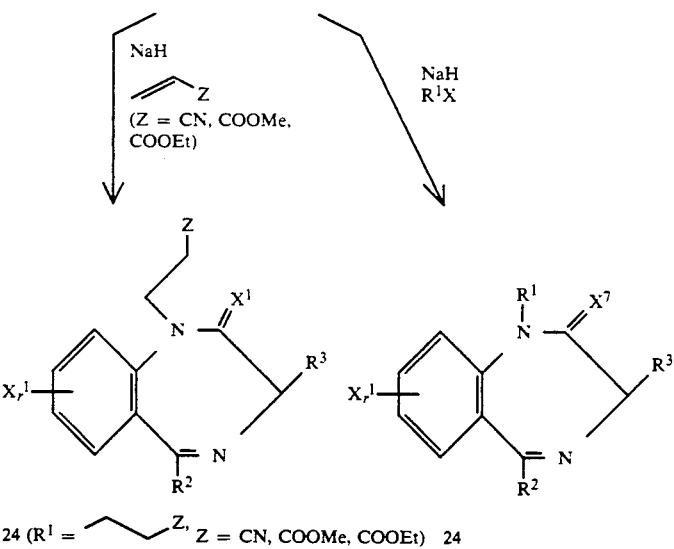
24 (R¹ = CH₂CH₂Z, Z = CN, COOMe, COOEt)   24
REACTION SCHEME IIId
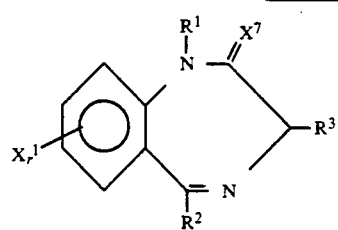

REACTION SCHEME IIId
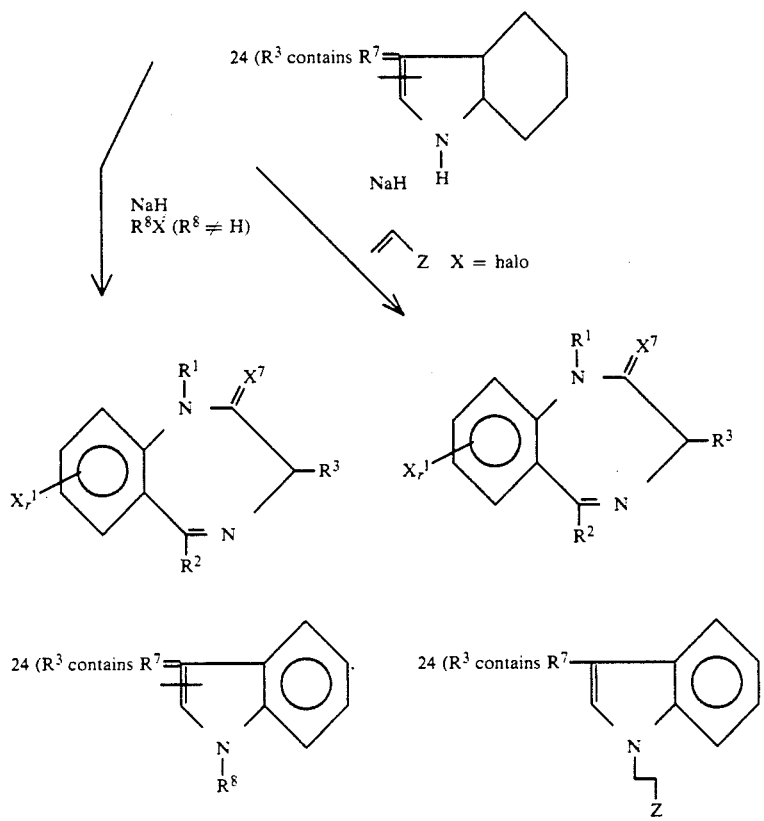
Where, in the 24 compound, $R^1$ and/or $R^8$ is an ester [$(X^{12})$COO—$C_1$-$C_3$ alkyl] moiety, this group can be conventionally hydrolyzed to obtain the corresponding acid moiety or treated with $NH_3$ to obtain the corresponding amide moiety.
REACTION SCHEME IV
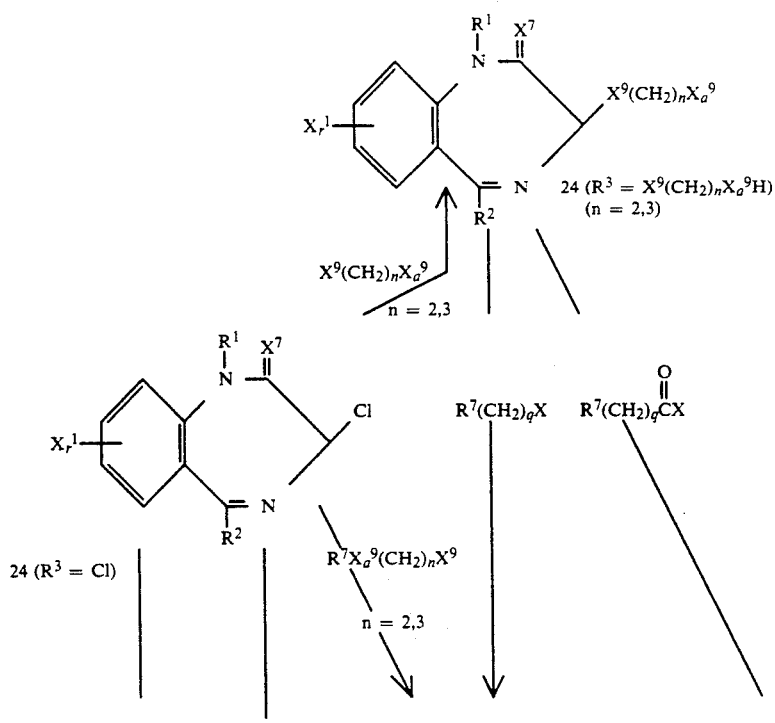

REACTION SCHEME IV
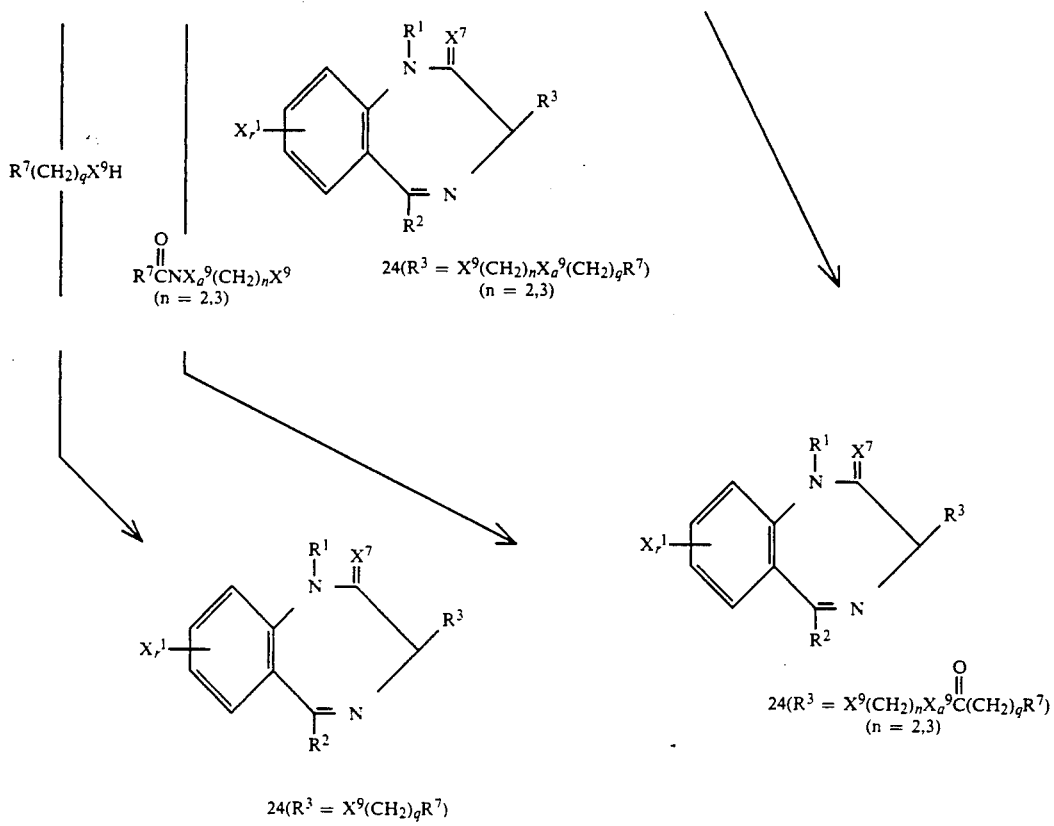
SCHEME IVa
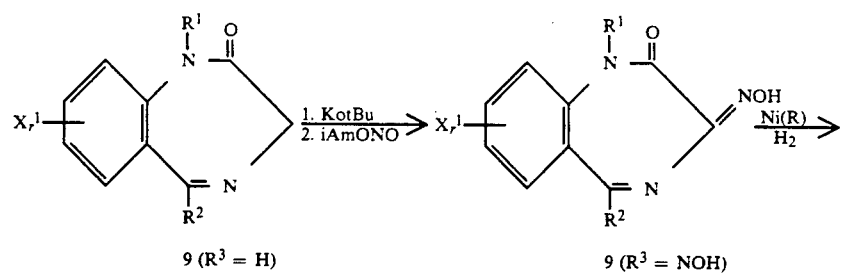
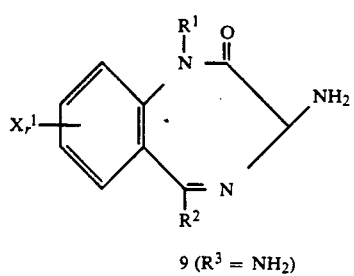

REACTION SCHEME V
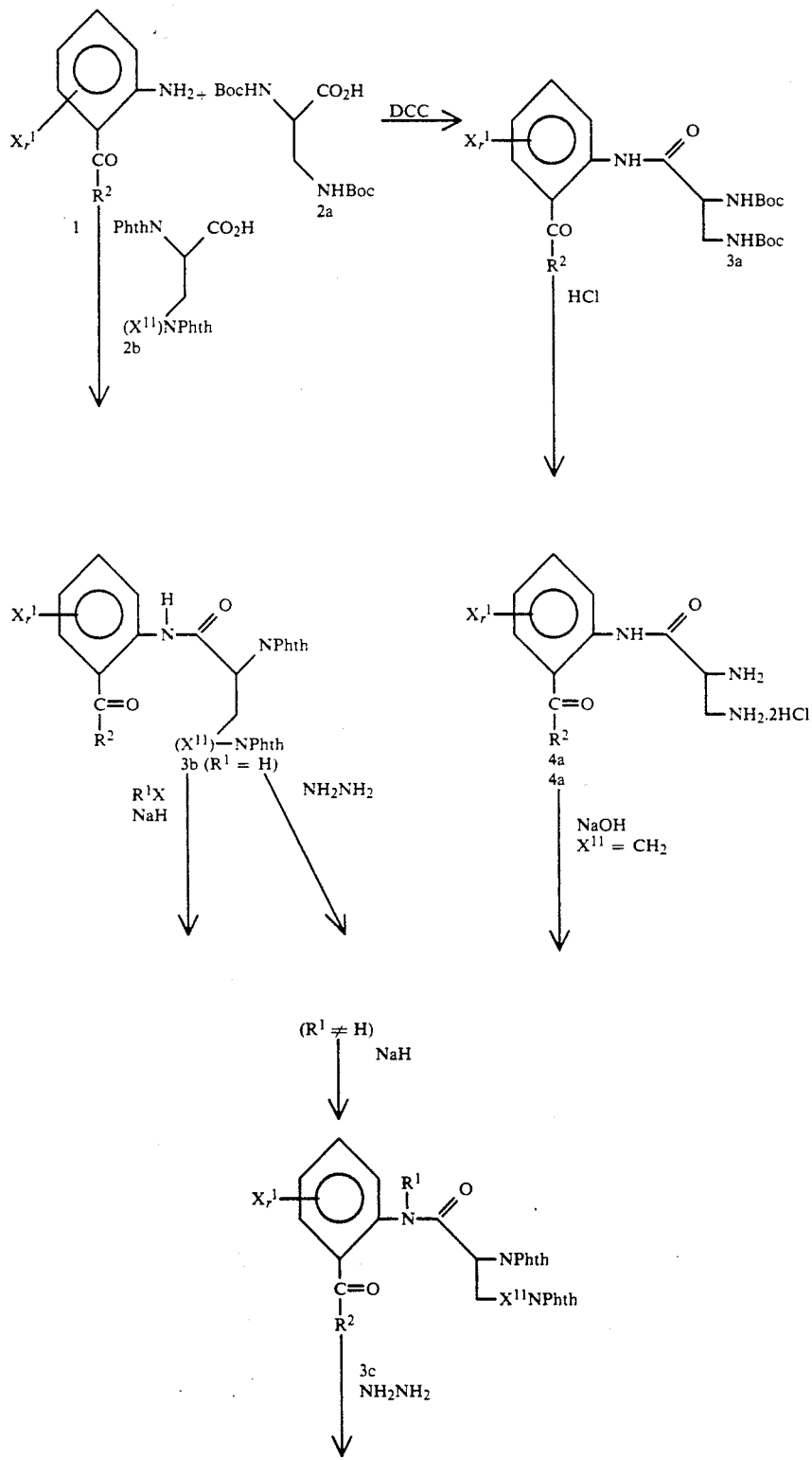

REACTION SCHEME V -continued
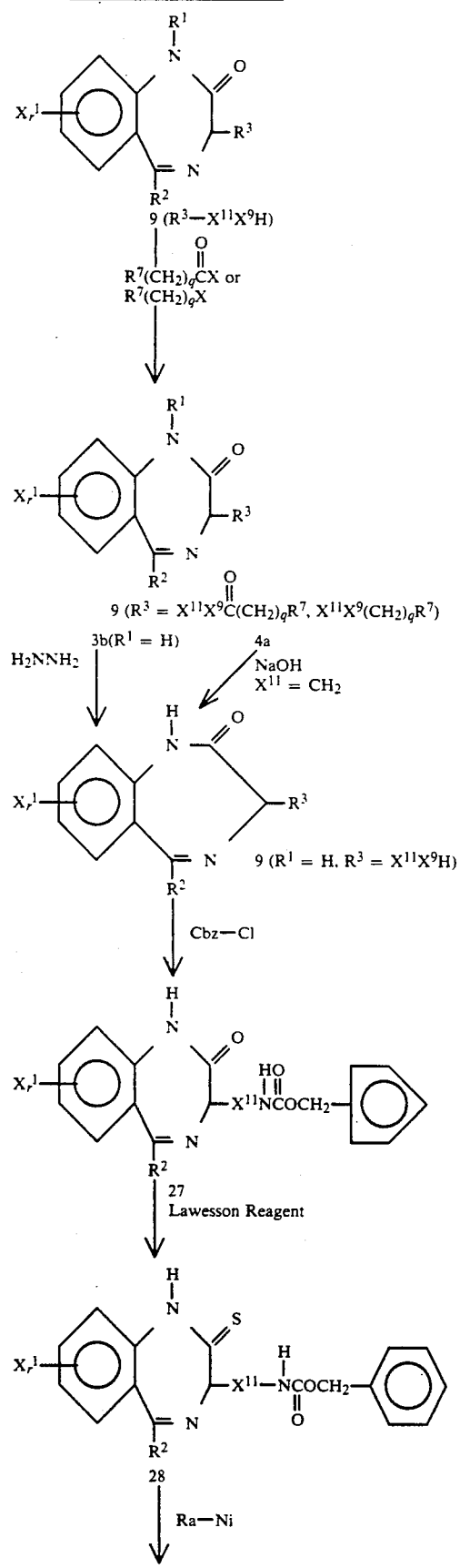

REACTION SCHEME V
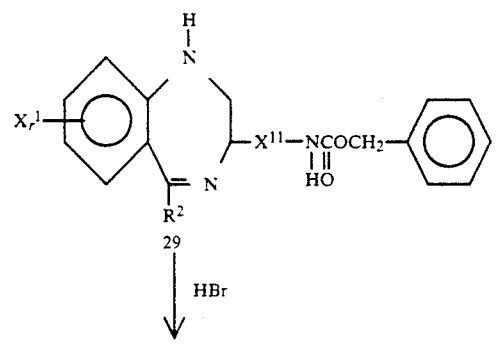
29
↓ HBr
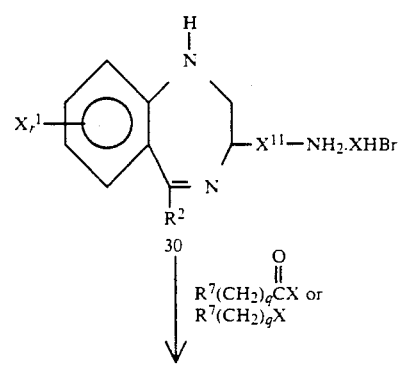
30
↓ R⁷(CH₂)qCX or
  R⁷(CH₂)qX
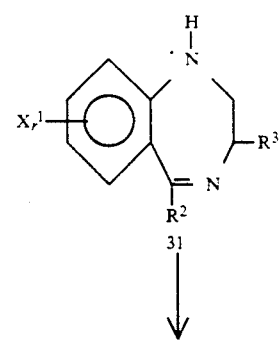
31
↓
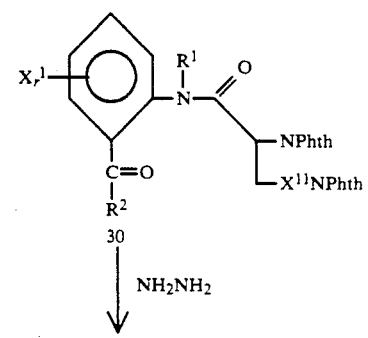
30
↓ NH₂NH₂

-continued
REACTION SCHEME V

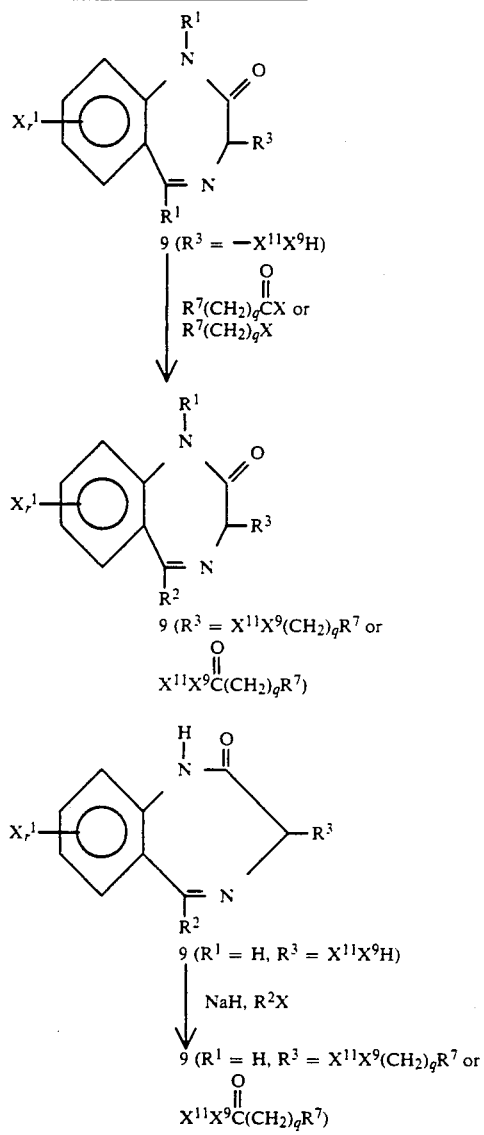

9 ($R^3 = -X^{11}X^9H$)

$$R^7(CH_2)_q\overset{O}{\underset{\|}{C}}X \text{ or}$$
$$R^7(CH_2)_qX$$

9 ($R^3 = X^{11}X^9(CH_2)_qR^7$ or
$X^{11}X^9\overset{O}{\underset{\|}{C}}(CH_2)_qR^7$)

9 ($R^1 = H$, $R^3 = X^{11}X^9H$)

NaH, $R^2X$ 9 ($R^1 = H$, $R^3 = X^{11}X^9(CH_2)_qR^7$ or
$X^{11}X^9\overset{O}{\underset{\|}{C}}(CH_2)_qR^7$)

2-Aminoarylketones 1, (Scheme I) preferably 2-amino-benzophenones containing various substituents in the aryl rings, preferably halo substituents, are coupled to N-protected D-amino acids 2 (preferably, Boc-amino acids) using dicyclohexylcarbodiimide (DCC) or other conventional peptide coupling reagent. The product 3 is N-deprotected by treatment with acid, preferably anhydrous HCl in ethyl acetate, to give the α-aminoacyl derivative 4 of the 2-aminoarylketone. Alternatively, this same product is obtained by treatment of the 2-aminoarylketone 1 with the acid chloride hydrochloride 5 of the D-amino acid, which is prepared from the amino acid with $PCl_5$—AcCl.

Treatment of this α-aminoacyl derivative 4 with base, preferably aqueous sodium hydroxide in methanol, gives the free base 6 which is cyclized to the 3,5-disubstituted benzodiazepine 7 upon stirring in the methanolic base for 2–120 hours, preferably 48 hours. Alternatively, the 3,5-disubstituted benzodiazepine 7 is obtained by heating the 2-aminoarylketone 1 with the ester 8, preferably methyl or ethyl, of the D-amino acid, preferably in refluxing pyridine, for 2–48 hours, preferably for 18 hours.

Alternatively (Scheme V), the ketones 1 may be coupled with N-phthalylamino acids such as 2b to give the products 3b using DCC or other conventional peptide coupling reagent. 3b may be deprotected and cyclized to 9 ($R^1$=H, $R^3$=$X^{11}X^9H$) by treating with hydrazine. Alternatively, 3b may be first alkylated by treatment with sodium hydride followed by an alkyl halide in dimethylformamide (DMF) to give the alkyl derivative 3c. Treating this product with hydrazine gives the $N^1$-alkylbenzodiazepine, 9 ($R^3$=$X^{11}X^9H$).

9 ($R^3$=$X^{11}X^9H$) are alkylated by treatment with alkyl halide or dialkyl sulfate or acylated by treatment with acid halides or anhydrides, preferably in the presence of base such as triethyl amine. The products are the alkyl and acyl derivatives 9 ($R^3$=$X^{11}X^9$ $(CH_2)_qR^7$ and $R^3$=

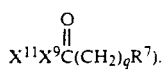

Alternatively, protection of the 3-amino function in 9 ($R^3=X^{11}NH_2$), preferably with benzylchloroformate affords the acyl derivative 27. Treatment of this material with $P_2S_5$ or preferably with Lawesson's reagent in toluene gives the thioamide 28 which is converted to the amine 29 with Raney nickel in ethanol. Deprotection of the resulting product 29 via hydrogenolysis, or preferably by the action of hydrobromic acid, yields the corresponding amino compound 30. Alkylation of 30 by treatment with alkyl halide or dialkyl sulfonate or acylation with carboxylic acid halide or carboxylic acid anhydride in the presence of an acid binding agent such as triethylamine or preferably with a carboxylic acid in the presence of a peptide coupling reagent such as dicyclohexyl-carbodiimide gives the alkyl or acyl derivatives 31.

3,5-Disubstituted benzodiazepines 7 (Scheme I) are also treated with sodium hydride in dimethylformamide (DMF), followed by an alkyl halide, to give the 1-alkyl derivatives 9. These or the parent 1-unsubstituted compound 7 are reduced, preferably with sodium cyanoborohydride and acetic acid at 15°., to give the corresponding 4,5-dihydro compounds 10. These are alkylated on $N_4$ by treatment with alkyl halide or dialkyl sulfate. Alternatively, the 4,5-dihydro compounds are acylated on $N_4$ by treatment with acyl halides or anhydrides, preferably in the presence of base such as triethylamine. The products are the alkyl and acyl derivatives 11. Alternatively, where $R^1$ is $-X^{12}COOR^6$ ($R^6$ not $=H$), 9 are treated with a base such as sodium hydroxide in methanol to give the acids 9 ($R^1=X^{12}COOH$).

The 3,5-disubstituted benzodiazepines 7 are treated with alkyl- or arylmagnesium halides, preferably methylmagnesium iodide, to give the dihydro compounds 12. The products are alkylated and acylated on nitrogen, as described for the 3,5-disubstituted-4,5-dihydro derivatives, to give the derivatives 13.

The 3,5-disubstituted benzodiazepines 7 are treated with $P_2S_5$ or Lawesson's reagent (2,4-bis-(4-methoxyphenyl)-2,4-dithioxo-1,3,2,4-dithiadiphosphetane) to give the 2-thiones 14. These are reduced with Raney nickel to the 2-unsubstituted compounds 15. The latter may be alkylated with alkyl halide or sulfate, acylated with acyl halide or anhydride, reduced with sodium cyanoborohydride, or substituted with alkyl- or aryl magnesium halide as described for 7 above.

Where the 3-position in a 3,5-disubstituted benzodiazepine 7 bears a substituent containing an indole moiety, preferably 3-indolylmethyl, reduction with triethylsilane/TFA provides the corresponding indoline 16. Alternatively, oxidation with HCl-dimethylsulfoxide provides the oxindole 17. 16 and 17 may be subjected to the reactions described for 7 to obtain alkyl, acyl, and dihydro derivatives. Dialkyl, alkylacyl, and trialkyl compounds may also be made using these methods.

The 3,5-disubstituted benzodiazepines 7 may also be oxidized, preferably with m-chloroperoxybenzoic acid, to give the corresponding 4-N-oxides 7a.

Alternatively, (Scheme II) 3-unsubstituted-5-substituted-1-substituted or unsubstituted benzodiazepines 9 ($R^1=H$) (Scheme II) prepared as described in the prior art may be treated with base, preferably lithium diisopropylamide, in an inert solvent, preferably THF, according to the procedure of J. Org. Chem., 46 4945 (1981). The resulting salt may be alkylated to obtain 9 with, for example, benzyl bromide or gramine methiodide. The resulting racemates may be resolved to obtain the preferred 3(R) enantiomers, or may be used as such.

Alternatively, the salt may be treated with an alkyl or aryl aldehyde, ketone, or acid halide or anhydride to give the 1-hydroxymethylene compounds 9

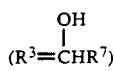

or 9

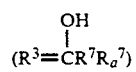

or the 1-ketomethylene derivatives 9

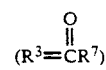

and 32

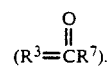

If the acid halide reaction is carried out in solvent containing peroxide, the 3- and 5-hydroxy analogs 20 and 21 (resp.) may be obtained.

The hydroxymethylene compounds 9

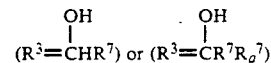

may be treated with acids, preferably trifluoroacetic acid, to obtain the olefins 18, 19, and/or 22.

Alternatively, 3-substituted benzodiazepines 9 may be obtained by treating the 3-unsubstituted compound 9 ($R^3=H$) with 1,8-diazabicyclo[5.4.0]undec-7-ene (DBU) and alkylating agent such as alkyl halide or sulfate or, preferably, gramine methiodide. Resolution to obtain the preferred 3(R) enantiomer may be carried out as described above.

3-Amino-5-substituted-1-substituted or unsubstituted benzodiazepines 9 ($R^3-NH_2$) are prepared as described in the prior art. Alternatively, 9 ($R^3=NH_2$) are prepared as shown in Scheme IVa. Treatment of the 3-unsubstituted compound 9 ($R^3=H$) with a suitable base, preferably potassium t-butoxide, followed by a nitrosating agent, preferably isoamyl nitrate, provides the oxime 9 ($R^3=NOH$). Reduction, preferably with Raney nickel, gives the 3-amino compounds 9 ($R^3=NH_2$). Alternatively, 9 ($R^3=NH_2$) are prepared by the method disclosed in U.S. Pat. No. 4,628,084.

3-Amino and 3-aminomethyl-5-substituted-1-substituted or unsubstituted benzodiazepines 23 (Scheme III) are alkylated with alkyl halides or with α-halo acids and esters to give the alkyl derivatives 24 ($R^3=X^{11}NH(CH_2)_qR^7$) and 9

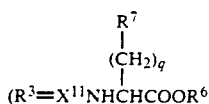

($R^3$=$X^{11}$NHCHCOOR$^6$)

With acyl halides, the amines 23 give the corresponding amides 24

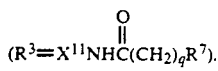

($R^3$=$X^{11}$NHC(CH$_2$)$_q$R$^7$).

With isocyanates, the amines 23 give the corresponding ureas 24

($R^3$=$X^{11}$NCN(CH$_2$)$_q$R$^7$).

With N-protected or unprotected α-amino acids and a coupling reagent such as DCC, EDC, or isobutyl chloroformate, the amines 23 give the amides 24

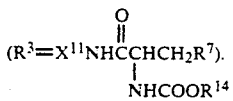

($R^3$=$X^{11}$NHCCHCH$_2$R$^7$).
NHCOOR$^{14}$

3-Hydroxy-5-substituted-7-substituted with sulfonyl chlorine, the amines 23 give the corresponding solfonamides 24 ($R^3$=$X^{11}$ NHSO$_2$(CH$_2$)qR$^7$) or unsubstituted-1-substituted or unsubstituted benzodiazepines 24 ($R^3$=OH) (Scheme IIIb) are acylated with acyl halides to give the esters 24

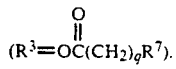

($R^3$=OC(CH$_2$)$_q$R$^7$).

3-Chloro-5-substituted-1-substituted or unsubstituted benzodiazepines 24 ($R^3$=Cl) (Scheme IV) may be used to monoalkylate amines to give the 3-substituted amino compounds 24 ($R^3$=NH$_2$). The 3-chloro compounds 29 may also be used to monoalkylate 1,2-ethanediamine and 1,3-propanediamine to give the compounds 24 ($R^3$=NH(CH$_2$)NH$_2$). These may be alkylated to provide 24 ($R^3$=NHX$^{11}$NH(CH$_2$)qR$^7$) or acylated to give 24

($R^3$=NHX$^{11}$NHC(CH$_2$)$_q$R$^7$).

Alternatively, the latter two compounds may be obtained from the previously mono-alkylated or acylated diamine and chloro compound 24 ($R^3$=Cl).

3-Substituted-5-substituted-7-substituted or unsubstituted benzodiazepines 24 ($R^1$=H) (Scheme IIIc) may be treated with sodium hydride in a suitable solvent, such as DNF, followed by an alkyl halide to provide the 1-alkyl derivatives 24. When an acrylate such as methyl or ethyl acrylate or acylonitrile is substituted for the alkyl halide, the 1-(2-substituted)ethyl compounds 24

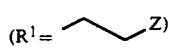

are obtained.

When $R^3$ contains $R^7$ where $R^7$ is 1-unsubstituted-2- or 3-indolyl (Scheme IIId), the compounds 24 may be further alkylated by treatment with sodium hydride followed by an alkyl halide or an acrylate, such as methyl or ethyl acrylate or acrylonitrile, or an activated amino acid such as Boc-phenylalanine anhydride to give the corresponding 1-substituted indole compounds 24 (Scheme IIId) in which $R^8$ is as defined herein and $R^8$ is other than hydrogen.

The compounds 24 wherein $R^1$ and/or $R^8$ is $X^{12}$—COOMe or $X^{12}$—COOEt may be treated with sodium hydroxide in an aqueous solvent, preferably aqueous solvent, preferably aqueous methanol, and then acidified to give the corresponding acids 24, wherein $R^1$ and/or $R^8$ is $X^{12}$COOH. Alternatively, these same compounds may be treated with aqueous or anhydrous ammonia to give the amides 24 wherein $R^1$ and/or $R^8$ is $X^{12}$CONH$_2$.

In cases where the starting materials are optically active, the chirality at $C_3$ is controlled by the synthesis. When racemic starting materials are employed, racemic products are obtained. The enantiomers may be separated by resolution.

The invention is further illustrated by reference to the following examples, which are not intended to be limiting of the claims

EXAMPLE 1

(+/−)-N-(2,3-DIHYDRO-1-METHYL-2-OXO-5-PHENYL-1H-1,4-BENZODIAZEPIN-3-YL)-N'-TRICYCLO(3.3.1.1(3,7))DEC-2-YL-UREA

Equimolar amounts of (R,S)-N-(2,3-dihydro-1,-methyl-2-oxo-5-phenyl-1H-1,4-benzodiazepin-3-yl)-p-nitrophenylcarbamate and (RS)-2-aminoadamantane were combined in DMF and treated with 1.1 equivalents of triethylamine. The reaction was stirred at 25° C. for 30 minutes. The DMF was removed in vacuo and the residue treated with H$_2$O and extracted with EtoAc (3×). The combined organics were washed with brine (1×), dried over Na$_2$SO$_4$, filtered and stripped to dryness in vacuo. The residue was flash chromatographed on silica gel (25% Et$_2$O in Et$_2$O CH$_2$Cl$_2$) and the title compared crystallized from ether: (mp 269°–270° C.).

TLC: Silica gel GF (180/10/1/1 CH$_2$Cl$_2$/MeOH/H$_2$O/EtoAc) Rf=0.42, single component.

$^1$HMNR: Consistent with structure.

HPLC: Greater then 97.2% pure.

Anal. Calcd for C$_{27}$H$_{30}$N$_4$O$_2$.0.1C$_4$H$_{10}$O: C, 73.13; H, 6.94; N, 12.45; Found: C, 72.99; H, 6.81; N, 12.45.

EXAMPLE 2

(+)-N-(2,3-DIHYDRO-1-METHYL-2-OXO-5-PHENYL-1H-1,4-BENZODIAZEPIN-3-YL)-N'-TRICYCLO(3.3.1.1(3,7))DEC-2-YL-UREA (+/−)-N-(2,3-dihydro-1-methyl-2-oxo-5-phenyl-1H-1,4-benzodiazepin-3-yl)-N'-tricyclo(3.3.1.1 (3,7))dec-2-yl-urea prepared as described in Example 1, was separated into its individual enantiomers by HPLC on a chiral support (SP 8100 Pirkle Covalent Phenylglycine Column (25×10 mm) using Hexane/2-propanol at 76:24 and a flow rate=6.0 ml/min) Component A (retention time=7.25 min) and component B (retention time=8.81 min) were isolated. The title compound was obtained by crystallization of component A from ether: (mp 272°–274° C.).

TLC: Silica gel GF (180/10/1/1 CH$_2$Cl$_2$/MeOH/H$_2$O/HoAc) Rf=0.41, single component.

$^1$HNMR: Consistent with structure.

HPLC: Greater then 99.9% pure.

Chiral Column HPLC: 95/5 mixture of enantiomers.

Anal. Calcd for C$_{27}$H$_{30}$N$_4$O$_2$: C, 73.27; H, 6.83; N, 12.66; Found: C, 73.29; H, 7.00; N, 12.60.

EXAMPLE 3

(R)-N-(2,3-DIHYDRO-1-METHYL-2-OXO-5-PHENYL-1H-1,4-BENZODIAZEPIN-3-YL)-N'-TRICYCLO(3.3.1.1 (3,7))DEC-1-YL-UREA

Equimolar amounts of 3(R)-amino-1,3-dihydro-1-methyl-5-phenyl-2H-1,4-benzodiazepin-2-one and adamantane-1-isocyanate were mixed in ethyl acetate and stirred at 25° C. for 72 hours. The resulting precipitate was collected by filtration to give the title compound: (mp 263.5°-265° C.).

TLC: Silica gel GF (10% acetone in CH$_2$Cl$_2$)Rƒ=0.51 single component.

$^1$HNMR: Consistent with structure.

HPLC: Greater then 99.2% pure.

Chiral Column HPLC: single enantiomer.

[α]p25D = +35.3° (3.6 mg/ml, CH$_3$OH).

Anal. Calcd for C$_{27}$H$_{30}$N$_4$O$_2$: C, 73.27; H, 6.83; N, 12.66; Found: C, 73.22; H, 6.84; N, 12.61.

EXAMPLE 4

(+/−)-N-(2,3-DIHYDRO-1-METHYL-2-OXO-5-PHENYL-1H-1,4-BENZODIAZEPIN-3-YL)-TRICYCLO(3.3.1.1(3,7))DECANE-1-CARBOXAMIDE

Equimolar amounts of 3(R,S)-amino-1,3-dihydro-1-methyl-5-phenyl-2H-1,4-benzodiazepin-2-one and adamantane-1-carboxylic acid chloride were mixed in methylene chloride. The pH was adjusted to 8.5 with triethylamine and the reaction stirred 10 mins at 25° C. The mixture was flash chromatographed on silica gel (5% Et$_2$O in Et$_2$O in Ch$_2$Cl$_2$CH$_2$CL$_2$) and the title compound obtained by trituration with ethyl acetate: (mp 256°-257° C.).

TLC: Silica gel GF (5% Et$_2$O in CH$_2$Cl$_2$) Rf=0.26, single component.

$^1$HNMR: Consistent with structure.

HPLC: Greater then 99.9% pure.

MS: Molecular ion at m/e=427.

Anal. Calcd for C$_{27}$H$_{29}$N$_3$O$_2$: C, 75.85; H, 6.84; N, 9.83; Found: C, 75.74; H, 7.12; N, 9.74.

EXAMPLE 5

(+/−)-N-(2,3-DIHYDRO-1-METHYL-2-OXO-5-PHENYL-1H-1,4-BENZODIAZEPIN-3-YL)-TRICYCLO(3.3.1.1(3,7))DECANE-1-ACETAMIDE)

3(R,S)-Amino-1,3-dihydro-1-methyl-5-phenyl 2H-1,4-benzodiazepin-2-one (75 mg, 0.283 mmols), 1-adamantylacetic acid (57.7 mg, 0.297 mmols), 1-hydroxybenzo triazole hydrate (40.2 mg, 0.297 mmols) and 1-ethyl-3-(3-dimethylaminopropyl)carbodiimide HCl (57.0 mg, 0.297 mmols) were combined in DMF (5 ml) and the pH adjusted to 9.5 with triethylamine. After stirring 5 hours, the DMF was removed in vacuo and the residue treated with H$_2$O, made basic with sat'd Na$_2$CO$_3$ (aq), and extracted with ethyl acetate (3×). The organic layers were combined, washed with H$_2$O and brine, dried over Na$_2$SO$_4$, filtered and stripped to dryness. The residue was flash chromatographed on silica gel (10% Et$_2$O in CH$_2$Cl$_2$) and the title compound crystallized from Et$_2$O: (mp 224°-225° C.).

TLC: Silica gel GF (10% Et$_2$O in CH$_2$Cl$_2$) Rf=0.31, single component.

$^1$HNMR: Consistent with structure.

HPLC: Greater then 99.3% pure.

MS: Molecular ion at m/e=441 (E.I.).

Anal. Calcd for C$_{28}$H$_{31}$N$_3$O$_2$: C, 76.16; H, 7.08; N, 9.52; Found: C, 76.49; H, 7.45; N, 9.51.

EXAMPLE 6

(+/−)-N-(2,3-DIHYDRO-1-METHYL-2-OXO-5-PHENYL-1H-1,4-BENZODIAZEPIN-3-YL)-N'-TRICYCLO(3.3.1.1(3,7))DEC-1-YL-METHYL)-UREA

Equimolar amounts of 3(R,S)-amino-1,3-dihydro-1-methyl-5-phenyl 2H-1,4-benzodiazepin-2-one and adamantane-1-methyl isocyanate were stirred in ethyl acetate at 25° C. for 15 hours. The solvent was removed and the crude product flash chromatographed on silica gel (8% acetone in CH$_2$Cl$_2$).

Crystallization from ether gave the title compound: (mp 228°-231° C.).

TLC: Silica gel GF (10% acetone in CH$_2$Cl$_2$) Rf=0.34, single component.

$^1$HNMR: Consistent with structure, ether observed.

HPLC: Greater then 99.8% pure.

Anal. Calcd for C$_{28}$H$_{32}$N$_4$O$_2$.0.1C$_4$H$_{10}$O: C, 73.51; H, 7.17; N, 12.08; Found: C, 73.36; H, 7.41; N, 12.11.

EXAMPLE 7

(+/−)-N-(2,3-DIHYDRO-1-METHYL-2-OXO-5-PHENYL-1H-1,4-BENZODIAZEPIN-3-YL)-3-METHYLTRICYCLO(3.3.1.1(3,7))DECANE-1-ACETAMIDE

The procedure of Example 5 was carried out using 3-methyl-1-adamantaneacetic acid (61.9 mg, 0.297 mmole) in place of 1-adamantylacetic acid. After work-up the residue was flash chromatographed on silica gel (7% Et$_2$O in CH$_2$Cl$_2$) and the title compound obtained by trituration with Et$_2$O: (mp 195°-196° C.). TLC: Silica gel GF (10% Et$_2$O in CH$_2$Cl$_2$), Rf=0.44 single component.

$^1$HNMR: Consistent with structure, ether observed.

HPLC: Greater than 97.3% pure.

Anal. Calcd for C$_{29}$H$_{33}$N$_3$O$_2$: C, 76.48; H, 7.30; N, 9.22; Found: C, 76.18; H, 7.24; N, 9.01.

EXAMPLE 8

(1S)-(1.ALPHA.(RS),4.ALPHA.))-N-(2,3-DIHYDRO-1-METHYL-2-OXO-5-PHENYL-1H-1,4-BENZODIAZEPIN-3-YL)-7,7-DIMETHYL-2-OXO-BICYCLO(2.2.1)HEPTANE-1-METHANESULFONAMIDE

3(R,S)-Amino-1,3-dihydro-5-phenyl-2H-1,4-benzodiazepin-2-one (75 mg, 0.283 mmols) and (+)-S-1-camphorsulfonyl chloride (78.0 mg, 0.311 mmols) were mixed in methylene chloride (3 ml) and the pH adjusted to 9.5 with triethylamine. The reaction was stirred at 25° C. for 30 minutes. A second portion of (+)-S-10-camphorsulfonyl chloride (30 mg, 0.120 mmol) was added followed by triethylamine to readjust the pH to 9.5 and the reaction stirred at 25° C. for 1 hour. The reaction was flash chromatographed on silica gel (10% Et$_2$O in CH$_2$Cl$_2$) and the title compound crystallized from ether/pet roleum ether: (mp 226°-227° C.).

TLC: Silica gel GF (10% Et₂O in CH₂Cl₂), Rf=0.41 single component.

¹HNMR: Consistent with structure.

HPLC: Greater then 99.5% pure, 1:1 mixture of diastereomers.

MS: Molecular ion at m/e=480 (M+H, FAB).

Anal. Calcd for $C_{26}H_{29}N_3O_4S$: C, 65.11; H, 6.10; N, 8:76; Found: C, 65.41; H, 6.15; N, 8.71.

EXAMPLE 9

(1R-(1.ALPHA.(RS),4.ALPHA.))-N-(2,3-DIHYDRO-1-METHYL-2-OXO-5-PHENYL-1H-1,4-BEN-ZODIAZEPIN-3-YL)-7,7-DIMETHYL-2-OXO-BICYCLO(2.2.1)HEPTANE-1-METHANESULFONAMIDE

The procedure of Example 8 was carried out using (−)-R-10-camphorsulfonyl chloride in place of the (+)-S-isomer. The product was isolated and purified as in Example 8: (mp 225°–226° C.).

TLC: Silica gel GF (10% Et₂O in CH₂Cl₂) Rf=0.38 single component.

¹HNMR: Consistent with structure.

HPLC: Greater than 99.6% pure, 1:1 mixture of diastereomers.

MS: Molecular ion at m/e=480 (M+H, FAB).

Anal. Calcd for $C_{26}H_{29}N_3O_4S$: C, 65.11; H, 6.10; N, 8.76; Found: C, 65.29; H, 6.15; N, 8.63.

EXAMPLE 10

(+/−)-N-(2,3-DIHYDRO-1-METHYL-2-OXO-5-PHENYL-1H-1,4-BENZODIAZEPIN-3-YL)-N'-TRICYCLO(3.3.1.0(3,7))DEC-2-YL-UREA

The procedure Example 1 was carried out using 3-amino-noradamantane in place of 2-amino adamantane. Flash chromatography on silica gel (15% Et₂O in CH₂Cl₂) followed by crystallization from ether gave the title compound: (mp 273°–276° C.).

TLC: Silica gel GF (20% Et₂O in CH₂Cl₂), Rf=0.44 single component.

¹HNMR: Consistent with structure, ether observed.

HPLC: Greater than 99.3% pure.

MS: Molecular ion at m/e=428 (E.I.).

Anal. Calcd for $C_{26}H_{28}N_4O_2.0.2\ C_4H_{10}O$: C, 72.60; H, 6.82; N, 12:64; Found: C, 72.51 H, 6.78; N, 12.79.

EXAMPLE 11

ALPHA.-((((2,3-DIHYDRO-1-METHYL-2-OXO-5-PHENYL-1H-1,4-BENZODIAZEPIN-3-YL)AMINO)CARBONYL)AMINO)BENZENEACETIC ACID ETHYL ESTER, ALPHA ISOMER

The procedure of example 1 was carried out using S-α-aminophenylacetic acid ethyl ester in place of 2-aminoadamantane. Flash chromatography on silica gel (EtOAc:Hexane, 1:1) afforded two diastereomers. Crystallization of the earlier eluted component from ether gave the title compound: (mp 181°–183° C.).

TLC: Silica gel GF (1:1 EtOAc/hexane) Rf=0.30 single component.

¹HNMR: Consistent with structure.

HPLC: 99.1% pure.

MS: Molecular ion at m/e=470 (E.I.).

Anal. Calcd for $C_{27}H_{26}N_4O_4$: C, 68.92; H, 5.57; N, 11:91; Found: C, 69.02; H, 5.57; N, 11.95.

EXAMPLE 12

(+/−)-1,2,3,5-TETRAHYDRO-1-METHYL-2-OXO-5-PHENYL-N-(TRICYCLO(3.3.1.1.(3,7))DEC-1-YLMETHYL)-4H-1,4-BENZODIAZEPINE-4-CARBOXAMIDE 1,3-Dihydro-1-methyl-5-phenyl-2H-1,4-benzodiazepin-2-one, (3.0 gm, 12.0 mmols) was dissolved in glacial acetic acid (20 ml), cooled to 10° C. in a cold water bath, and treated with sodium cyanoborohydride (1.51 gm, 24.0 mmols) in 5 equal portions over 5 minutes. The reaction mixture was stirred 20 minutes, then poured into water (40 ml), basified with sat'd Na₂CO₃(aq) and extracted with EtoAc (3×). The combined extracts were washed with brine (1×), dried over Na₂SO₄, and stripped to dryness in vacuo. The residue was crystalized from ether to give compound A.

Equimolar amounts of compound A and adamantane-1-methyl isocyanate were mixed in ethyl acetate and stirred overnight. The solvent was removed in vacuo and the residue flash chromatographed on silica gel (7% acetone in CH₂Cl₂). Crystallization from ethyl acetate gave the title compound: (mp 242°–244° C.).

TLC: Silica gel GF (7% acetone in CH₂Cl₂) Rf=0.31 single component.

¹HNMR: Consistent with structure, EtoAc observed.

HPLC: 99.9% pure.

MS: Molecular ion at m/e=443 (E.I.).

Anal. Calcd for $C_{28}H_{33}N_3O_2.0.2\ C_4H_8O_2$: C, 75.00; H, 7.56; N, 9:11; Found: C, 74.81; H, 7.56; N, 9.18.

EXAMPLE 13

(+/−)-1,2,3,5-TETRAHYDRO-1-METHYL-2-OXO-5-PHENYL-N-TRICYCLO(3.3.1.1(3,7))DEC-2-YL-4H-1,4-BENZODIAZEPINE-4-CARBOXAMIDE

Equimolar amounts of compound A prepared in Example 12 and adamantane-2-isocyanate were mixed in ethyl acetate and stirred overnight. The solvent was removed in vacuo and the residue flash chromatographed on silica gel (7% acetone in CH₂Cl₂). Crystallization from ethyl acetate gave the title compound: (mp 243°–244° C.).

TLC: Silica gel GF (7% acetone in CH₂Cl₂) Rf=0.25, single component.

¹HNMR: Consistent with structure.

HPLC: 99.9% pure.

MS: Molecular ion at m/e=429 (E.I.).

Anal. Calcd for $C_{27}H_{31}N_3O_2$: C, 75.49; H, 7.27; N, 9:78; Found: C, 75.13; H, 7.25; N, 9.66.

EXAMPLE 14

(1R-(1.ALPHA.(R*),4.ALPHA.))-N-(2,3-DIHYDRO-1-METHYL-2-OXO-5-PHENYL-1H-1,4-BENZODIAZEPIN-3-YL)-7,7-DIMETHYL-2-OXO-BICYCLO(2.2.1)HEPTANE-1-METHANESULFONAMIDE

The procedure of example 8 was carried out using 3(S)-amino-1,3-dihydro-5-phenyl-2H-1,4-benzodia zepin-2-one in place of the 3(RS) compound, and (−)-R-10-camphorsulfonyl chloride in place of the (+)-(S) isomer. The product was isolated and purified as described in Example 8: (mp 204°–206° C.).

TLC: Silica gel GF (10% EtoAc in CH₂Cl₂), Rf=0.38, single component.

¹HNMR: Consistent with structure.

HPLC: Greater than 98.7% pure, 10:1 mixture of diastereomers.

MS: Molecular ion at m/e=479 (E.I.).

Anal. Calcd for $C_{26}H_{29}N_3O_4S$: C, 65.11; H, 6.10; N, 8.76; Found: C, 65.50; H, 6.31; N, 8.66.

EXAMPLE 15

(1R-(1.ALPHA.(S*),4.ALPHA.))-N-(2,3-DIHYDRO-1-METHYL-2-OXO-5-PHENYL-1H-1,4-BENZODIAZEPIN-3-YL)-7,7-DIMETHYL-2-OXO-BICYCLO(2.2.1)HEPTANE-1-METHANESULFONAMIDE

The product of Example 14 was carried using 3-(R)-amino-1,3-dihydro-5-phenyl-2H-1,4-benzodiazepin-2-one in place of the 3(S) isomer. The product was isolated as described in Example 14: (mp 213°–214.5° C.).

TLC: Silica gel GF (10% $Et_2O$ in $CH_2Cl_2$) Rf=0.38, single component.

$^1$HNMR: Consistent with structure.

HPLC: Greater than 99% pure, 92:8 mixture of diastereomers.

MS: Molecular ion at m/e=479 (E.I.).

Anal. Calcd for $C_{26}H_{29}N_3O_4S$: C, 65.11; H, 6.10; N, 8.76; Found: C, 65.47; H, 6.28; N, 8.69.

EXAMPLE 16

N-(2,3-DIHYDRO-1-METHYL-2-OXO-5-PHENYL-1H-1,4-BENZODIAZEPIN-3-YL)-2-HYDROXY-7,7-DIMETHYL-BICYCLO(2.2.1)HEPTANE-1-METHANESULFONAMIDE, ISOMER A AND ISOMER B (1R-(1.Alpha.(S*),4.alpha.))-N-(2,3-dihydro-1-methyl-2-oxo-5-phenyl-1H-1,4-benzodiazepin-3-yl)-7,7-dimethyl-2-oxo-bicyclo(2.2.1)heptane-1-methanesulfonamide was suspended in absolute ethanol and treated with 2 equivalents of sodium borohydride. The reaction was stirred at 25° C. for 16 hours and the solvent removed in vacuo. The residue was treated with 10% $NaHCO_3$(aq) and extracted with ether (3×). The combined organics were washed with brine (1×), dried over $Na_2SO_4$, filtered and stripped to dryness in vacuo. Flash chromatography of the crude mixture on silica gel (7% $Et_2O$ in $CH_2Cl_2$) afforded two products, Isomer A the faster eluted and Isomer B the slower. These were evaporated individually to dryness.

Isomer A: Recrystallization form ether/hexane provided Isomer A of the title compound: (mp 93°–144° C.).

TLC: Silica gel GF (10% $Et_2O$ in $CH_2Cl_2$), Rf=0.40, single component.

$^1$HNMR: Consistent with structure.

HPLC: two components (Isomer A: Isomer B=83:17).

MS: Molecular ion at m/e=481 (E.I.).

Anal. Calcd for $C_{26}H_{31}N_3O_4S$: C, 64.84; H, 6.49; N, 8.73; Found: C, 64.76; H, 8.76; N, 8.63.

Isomer B: Recrystallization form ether provided Isomer B of the title compound: (mp 239°–240° C.).

TLC: Silica gel GF (10% $Et_2O$ in $CH_2Cl_2$), Rf=0.28, single component.

$^1$HNMR: Consistent with structure.

HPLC: Four components 39:10:9:42.

MS: Molecular ion at m/e=481 (E.I.).

Anal. Calcd for $C_{26}H_{31}N_3O_4S$: C, 64.84; H, 6.49; N, 8.73; Found: C, 64.72; H, 6.59; N, 8.60.

EXAMPLE 17

N-(2,3-DIHYDRO-1-METHYL-2-OXO-5-PHENYL-1H-1,4-BENZODIAZEPIN-3-YL)-2-HYDROXY-7,7-DIMETHYL-BICYCLO(2.2.1)HEPTANE-1-METHANESULFONAMIDE

The procedure of Example 16 was carried out using (1R-(1.alpha.(R*),4.alpha.))-N-(2,3-dihydro-1-methyl-2-oxo-5-phenyl-1H-1,4-benzodiazepin-3-yl)-7,7-dimethyl-2-oxo-bicyclo(2.2.1)heptane-1-methanesulfonamide in place of the (1R-(1.ALPHA.(S*)-isomer. Chromatography of the crude mixture on silica gel (10% $Et_2O$ in $CH_2Cl_2$) afforded an incompletely separated isomer mixture. Evaporation to dryness and crystallization from ether gave the title compound as a 1:1 mixture of isomers: (mp 229°–231° C.).

TLC: Silica gel GF (10% $Et_2O$ in $CH_2Cl_2$), Rf=0.38, 0.28; 1:1 mixture of two components.

$^1$HNMR: Consistent with structure.

HPLC: Two components, 48:51.

MS: Molecular ion at m/e=481 (E.I.).

Anal. Calcd for $C_{26}H_{31}N_3O_4S$: C, 64.84; H, 6.49; N, 8.73; Found: C, 64.78; H, 6.47; N, 8.64.

EXAMPLE 18

[3(S)-N-(2,3-DIHYDRO-1-METHYL-2-OXO-5-PHENYL-1H-1,4-BENZODIAZEPIN-3-YL)]-2-OXO-1,7,7-TRIMETHYL-BICYCLO(2.2.1)HEPTANE-3-ACETAMIDE

The procedure of Example 5 was carried out using 3-(S)-amino-1,3-dihydro-5-phenyl-2H-1,4-benzodiazepin-2-one in place of the 3-(RS)compound, and (+)-camphoracetic acid in place of 1-adamanteylacetic acid. Flash chromatography on silica gel (30% $ET_2O$ in $CH_2Cl_2$) and crystallization from cyclohexane gave the title compound: (mp 102°–116° C.).

TLC: Silica gel GF (30% $Et_2O$ in $CH_2Cl_2$); Rf=0.49, single component.

$^1$HNMR: Consistent with structure, cyclohexane observed.

HPLC: 92:8 mixture of diastereomers.

MS: Molecular ion at m/e=457 (E.I.).

Anal. Calcd for $C_{28}H_{31}N_3O_3 \cdot 0.45 \, C_6H_{14}$: C, 74.42; H, 7.41; N, 8.48; Found: C, 74.35; H, 7.55; N, 8.24.

EXAMPLE 19

[3(R)-N-(2,3-DIHYDRO-1-METHYL-2-OXO-5-PHENYL-1H-1,4-BENZODIAZEPIN-3-YL)]-2-OXO-1,7,7-TRIMETHYL-BICYCLO(2.2.1)HEPTANE-3-ACETAMIDE

The procedure of Example 18 was carried out using 3-(R)-amino-1,3-dihydro-5-phenyl-2H-1,4-benzodiazepin-2-one in place of the 3-(S) enantiomer. The title compound was isolated and purified as described in Example 18: (mp 118°–120° C.).

TLC: Silica gel GF (30% $Et_2O$ in $CH_2Cl_2$); Rf=0.36, diastereomers observed.

$^1$HNMR: Consistent with structure, cyclohexane observed.

HPLC: 92:8 mixture of diastereomers.

MS: Molecular ion at m/e=457 (E.I.).

Anal. Calcd for $C_{28}H_{31}N_3O_3 \, 0.4 \, C_6H_{14}$: C, 74.32; H, 7.35; N, 8.55; Found: C, 74.00; H, 7.48; N, 8.22.

EXAMPLE 20

(1S-(1.ALPHA.(S*),4.ALPHA.))-N-(2,3-DIHYDRO-1-METHYL-2-OXO-5-PHENYL-1H-1,4-BENZODIAZEPIN-3-YL)-7,7-DIMETHYL-2-OXO-BICYCLO(2.2.1)HEPTANE-1-METHANESULFONAMIDE

The procedure of Example 15 was carried out using (+)-S-10-camphorsulfonyl chloride in place of the (−)-R-enantiomer. The product was isolated and purified as described in Example 15: (mp 199°–204° C.).

TLC: Silica gel GF (10% EtO in CH$_2$Cl$_2$), Rf=0.44, single component.

$^1$HNMR: Consistent with structure.
HPLC: 99:1 mixture of diastereomers.
MS: Molecular ion at m/e=479 (E.I.).
Anal. Calcd for C$_{26}$H$_{29}$N$_3$O$_4$S: C, 65.11; H, 6.10; N, 8.76; Found: C, 65.30; H, 6.15; N, 8.69.

EXAMPLE 21

(1S-(1.ALPHA.(R*), 4.ALPHA.))-N-(2,3-DIHYDRO-1-METHYL-2-OXO-5-PHENYL-1H-1,4-BENZODIAZEPIN-3-YL)-7,7-DIMETHYL-2-OXO-BICYCLO(2.2.1)HEPTANE-1-METHANESULFONAMIDE

The procedure of Example 14 was carried out using (+)-S-10-camphorsulfonyl chloride in place of the (−)-R-enantiomer. The product was isolated and purified as described in Example 14: (mp 219°–220° C.).

TLC: Silica gel GF (10% Et$_2$O in CH$_2$Cl$_2$), Rf=0.41, single component.

$^1$HNMR: Consistent with structure.
HPLC: 98:2 mixture of diastereomers.
MS: Molecular ion at m/e=479 (E.I.).
Anal. Calcd for C$_{26}$H$_{29}$N$_3$O$_4$S: C, 65.11; H, 6.10; N, 8.76; Found: C, 65.12; H, 6.01; N, 8.78.

EXAMPLE 22

[3(S)-N-(2,3-DIHYDRO-1-METHYL-2-OXO-5-PHENYL-1H-1,4-BENZODIAZEPIN-3-YL)]-2-HYDROXY-1,7,7-TRIMETHYL-BICYCLO(2.2.1)HEPTANE-3-ACETAMIDE, ISOMER A AND ISOMER B

3(S)-N-(2,3-Dihydro-1-methyl-2-oxo-5-phenyl-1H-1,4-benzodiazepin-3-yl)]-2-oxo-1,7,7-trimethylbicyclo(2.2.1)heptane-3-acetamide was dissolved in abs. ethanol and treated with 2 equivalents of sodium borohydride. The reaction was stirred at 25° C. for 60 hours and the solvent removed in vacuo. The residue was treated with 10% NaHCO$_3$(aq) and extracted with Et$_2$O (3×). The organics were combined and washed with brine (1×), dried over Na$_2$So$_4$, filtered and stripped to dryness. Flash chromatography of the crude mixture on silica gel (9% acetone in CH$_2$Cl$_2$) afforded two products, Isomer B the earlier eluted, and Isomer A the later eluted. These were evaporated individually to dryness.

Isomer B: Lyophilization from dioxane/water provided Isomer B of the title compound: (mp 160°–165° C.).

TLC: Silica gel GF (10% acetone in CH$_2$Cl$_2$), Rf=0.36, single component.

$^1$HNMR: Consistent with structure, dioxane observed.

HPLC: 11:1 mixture of diastereomers, 93% overall purity.

MS: Molecular ion at m/e=460 (M+H, FAB).
Anal. Calcd for C$_{28}$H$_{33}$N$_3$O$_3$.0.3 C$_4$H$_8$O$_2$: C, 72.15; H, 7.34; N, 8.65; Found: C, 72.40; H, 7.43; N, 8.29.

Isomer A: Recrystallization from ether provided Isomer A/of the title compound: (mp 202°–204° C.).

TLC: Silica gel GF (10% acetone in CH$_2$Cl$_2$) Rf=0.27, single component.

$^1$HNMR: Consistent with structure, H$_2$O observed.
HPLC: Greater than 96% pure.
MS: Molecular ion at m/e=460 (M+H FAB).
Anal. Calcd for C$_{28}$H$_{33}$N$_3$O$_3$.0.15 H$_2$O: C, 72.74; H, 7.26; N, 9.09; Found: C, 72.57; H, 7.07; N, 9.01.

EXAMPLE 23

[3(R)-N-(2,3-DIHYDRO-1-METHYL-2-OXO-5-PHENYL-1H-1,4-BENZODIAZEPIN-3-YL)]-2-OXO-1,7,7-TRIMETHYLBICYCLO(2.2.1)HEPTANE-3-CARBOXAMIDE

3(R)-Amino-1,3-dihydro-5-phenyl-2H-1,4-benzodiazepin-2-one (170 mg, 0.641 mmol), (−)-Camphorcarboxylic acid (138 mg, 0.705 mmol), 1-hydroxybenzotriazole hydrate (95.3 mg, 0.705 mmol) and 1-ethyl-3-(3-dimethylaminopropyl) carbodiimide hydrochloride (EDC, 135 mg, 0.705 mmol) were combined in freshly degassed DMF (3 ml) and the pH of the solution was adjusted to 9.5 with triethylamine (115 μl). After stirring 1 hour at 25° C., the DMF was removed in vacuo, the residue treated with H$_2$O and extracted with EtoAc (3×). The combined organic layers were washed with brine, dried over Na$_2$SO$_4$, filtered and stripped to dryness. The crude product was flash chromatographed on silica gel (10% Et$_2$O in CH$_2$Cl$_2$) and the title compound was obtained as a crystalline solid from ether: (mp 196°–197° C.).

TLC: Silica gel GF (10% Et$_2$O in CH$_2$Cl$_2$), Rf=0.31, single component.

$^1$HNMR: Consistent with structure, diastereomer mixture observed.

HPLC: Greater than 93% pure (6% diastereomer).
MS: Molecular ion at m/e=443 (E.I.).
Anal. Calcd for C$_{27}$H$_{29}$N$_3$O$_3$: C, 73.11; H, 6.59; N, 9.47; Found: C, 73.44; H, 6.65; N, 9.51.

IN VITRO ACTIVITY OF COMPOUNDS OF FORMULA I

The biological activities of the compounds of Formula I have been evaluated using a[$^3$H]oxytocin binding assay.

[$^3$H]Oxytocin Binding Assay

Oxytocin receptors have been identified in mammalian uterine tissue through the use of in vitro radioligand binding assays. These receptor binding sites mediate the contractile response of the uterine myometrium to oxytocin. The present radioligand binding procedure has been adapted from the methods of Soloff, M. S. and Grzonka, Z., *Endocrinology* 119: 1564–1569 (1986) and Fuchs, A-R., Fuchs, F., and Soloff, M. S., *J. Clinical Endocrinology and Metabolism* 60: 37–41 (1985) and is utilized here to measure the relative affinity of test compounds for the oxytocin receptor labeled by [$^3$H]oxytocin. The assay uses a crude membrane preparation of rat uterus as the source of oxytocin receptors. The IC$_{50}$ values (concentration of test compound to inhibit [$^3$H]oxytocin binding by 50%) are determined by incubating uterine tissue with [$^3$H]oxytocin in the presence or absence of varying concentrations of compound.

TABLE III

| Potencies of Compounds in Oxytocin Binding Assays | | |
|---|---|---|
| Compound of | [³H]OT(uterus) | |
| Example | IC$_{50}$(μM) | % inhibition @ μM conc. |
| 1 | 3.9 | |
| 2 | 1.6 | |
| 3 | 1.69 | |
| 4 | 13.8 | |
| 5 | 2.8 | |
| 6 | 2.7 | |
| 7 | 4.7 | |
| 8 | 4.6 | |
| 9 | 3.6 | |
| 10 | 2.7 | |
| 11 | | 46% @ 10 |
| 12 | | 66% @ 10 |
| 13 | | 48% @ 10 |
| 14 | | 52% @ 10 |
| 15 | 1.4 | |
| 16A | 1.4 | |
| 16B | 1.0 | |
| 17 | 2.5 | |
| 18 | | 39% @ 10 |
| 19 | | 82% @ 10, 39 @ 1 |
| 20 | | 80% @ 10, 35% @ 1 |
| 21 | | 15% @ 10 |
| 22A | | 50% @ 10 |
| 22B | | 41% @ 10 |
| 23 | | 85% @ 10, 35% @ 1 |

What is claimed is:

1. A compound of the formula:

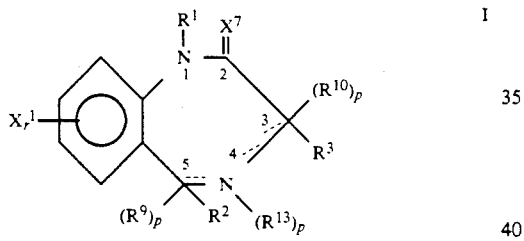

wherein $R^1$ is H, $C_1$–$C_6$ linear or branched alkyl, loweralkenyl, lower alkynyl, —$X^{12}COOR^6$, —$X^{11}$-lower cycloalkyl, —$X^{12}CN$, or —$X^{11}CX_3^{10}$;

$R^2$ is H, loweralkyl, substituted or unsubstituted phenyl (wherein the substitutents may be 1 or 2 of halo, loweralkyl, loweralkoxy, loweralkylthio, carboxyl, carboxyloweralkyl, nitro, —$CF_3$, or hydroxy), 2-, 3-, 4-pyridyl,

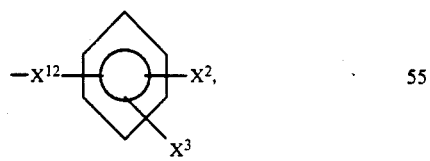

—$X^{12}SCH_3$, —$x^{12}SOCH_3$, —$X^{12}SO_2CH_3$, or —$X^{12}COOR^6$;

$R^3$ is H, —$X^{11}NR^{18}X_a^{11}R^7$,

—$NHX^{11}NHR^7$, —$NHX^{11}NHCOR^7$,

-continued $$-X^{11}\overset{O}{\underset{\|}{C}}X^9X_a^{11}R^7,$$

$$-X^{11}X^9\overset{\nearrow O}{C}CHX_a^{11}R^7, \quad -X^{11}X^9\overset{O}{\underset{\|}{C}}NHCH-COOR^{14},$$
$$\underset{NHCOOR^{14},}{} \qquad \underset{R^6}{}$$

$$-X^{11}NR^{18}\overset{O}{\underset{\|}{C}}X_a^9X^{11}R^7,$$

$$-X^{11}X^9C-CH-X_a^{11}R^7,$$
$$\underset{\|}{O}\ \underset{|}{NH_2}$$

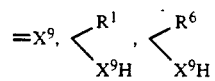

—$X^{11}NR^{18}SO_2X_a^{11}R^7$ or —$X^{11}\overset{O}{\underset{\|}{C}}R^7$, $R^6$ is H, loweralkyl, lower cycloalkyl, substituted or unsubstituted phenyl, or substituted or unsubstituted phenylloweralkyl wherein the phenyl or phenylloweralkyl substituents may be 1 or 2 of halo, loweralkyl, loweralkoxy, nitro, or $CF_3$;

$R^7$ is loweralkyl, lower cycloalkyl, $X^{12}$-cycloloweralkyl, wherein lower cycloalkyl encompasses $C_3$–$C_{10}$ and may be mono or polycyclic, including bridged units, and such lower cycloalkyl units may be unsubstituted or independently substituted at one or two of the secondary carbons with the following substituents:

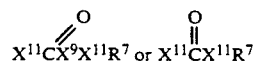

$R^9$ and $R^{10}$ are independently H, —OH, or —$CH_3$;
$R^{13}$ is H, loweralkyl, carboxyl, O, cycloloweralkyl,

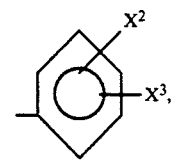

$R^{14}$ is loweralkyl or phenylloweralkyl;
$R^{15}$ is H, loweralkyl, or —$NH_2$;
$R^{18}$ is H, OH, $OR^{13}$, or loweralkyl;
p is O when its adjacent is unsaturated and 1 when its adjacent is saturated except that when $R^{13}$ is O, p=1 and is unsaturated;
r is 1 or 2;
$X^1$ is H, —$NO_2$, $CF_3$ CN, OH, loweralkyl, halo, loweralkylthio, loweralkoxy, —$X^{11}COOR^6$, or —$X^{11}NR^4R^5$;

$X^2$ and $X^3$ are independently H, —OH, —$NO_2$, halo, loweralkylthio, loweralkyl, or loweralkoxy;

$X^7$ is O, S, HH, or $NR^{15}$ with the proviso that $X^7$ can be $NR^{15}$ only when $R^1$ is not H;

$X^9$ and $X_a^9$ are independently $NR^{18}$ or O;

$X^{10}$ is F, Cl, or Br;

$X^{11}$ and $X_a^{11}$ are independently absent or $C_{1-4}$ linear or branched alkylidene; $X^{12}$ os $C_{1-4}$ linear or branched alkyl;

is a saturated or unsaturated bond;

and the pharmaceutically acceptable salts thereof, with the proviso that $R^3$ is H when and only when $R^{13}$ is

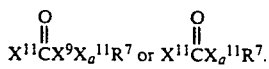

2. A compound of claim 1 wherein: wherein:

$R^1$ is H, $C_1$-$C_6$ linear or branched alkyl;

$R^2$ is substituted or unsubstituted phenyl (wherein the substituents may be 1 or 2 of halo, loweralkyl, loweralkoxy, loweralkylthio, carboxyl, carboxyloweralkyl, nitro, —$CF_3$, or hydroxy);

$R^3$ is —$X^{11}NR^{18}X_a^{11}R^7$,

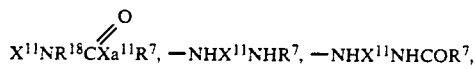

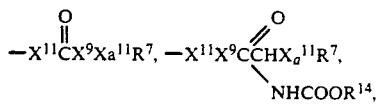

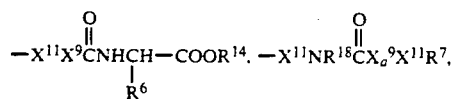

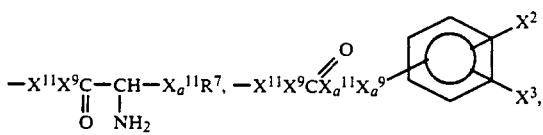

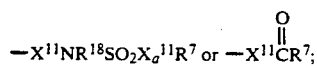

$R^6$ is H, loweralkyl, lower cycloalkyl, substituted or unsubstituted phenyl, or substituted or unsubstituted phenylloweralkyl wherein the phenyl or phenylloweralkyl substituents may be 1 or 2 of halo, loweralkyl, loweralkoxy, nitro, or $CF_3$;

$R^7$ is loweralkyl, lower cycloalkyl, $X^{12}$-lower cycloalkyl, wherein lower cycloalkyl encompasses $C_3$-$C_{10}$ and may be mono or polycyclic, including bridged units, and such cycloloweralkyl units may be unsubstituted or independently substituted at one or two of the secondary carbons with the following substituents:

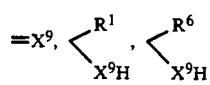

$R^9$ and $R^{10}$ are independently H;

$R^{13}$ is H;

$R^{14}$ is loweralkyl or phenylloweralkyl;

$R^{15}$ is H, loweralkyl,

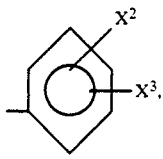

or —$NH_2$;

$R^{18}$ is H, OH, or loweralkyl;

p is 0 when its adjacent    is unsaturated and 1 when its adjacent    is saturated;

r is 1;

$X^1$ is H;

$X^7$ is O;

$X^9$ and $X_a^9$ are independently $NR^{18}$ or O;

$X^{11}$ and $X_a^{11}$ are independently absent or $C_{1-4}$ linear or branched alkyl;

$X^{12}$ is $C_{1-4}$ linear or branched alkyl is a saturated or unsaturated bond;

and the pharmaceutically acceptable salts thereof.

3. A compound selected from the group consisting of:

(+/−)-N-(2,3-DIHYDRO-1-METHYL-2-OXO-5-PHENYL-1H-1,4-BENZODIAZEPIN-3-YL)-N'-TRICYCLO(3.3.1.1(3,7))DEC-2-YL-UREA (+)-N-(2,3-DIHYDRO-1-METHYL-2-OXO-5-PHENYL-1H-1,4-BENZODIAZEPIN-3-YL)-N'-TRICYCLO(3.3.1.1(3,7))DEC-2-YL-UREA (R)-N-(2,3-DIHYDRO-1-METHYL-2-OXO-5-PHENYL-1H-1,4-BENZODIAZEPIN-3-YL)-N'-TRICYCLO(3.3.1.1(3,7))DEC-1-YL-UREA (+/−)-N-(2,3-DIHYDRO-1-METHYL-2-OXO-5-PHENYL-1H-1,4-BENZODIAZEPIN-3-YL)-TRICYCLO(3.3.1.1(3,7))DECANE-1-CARBOXAMIDE (+/−)-N-(2,3-DIHYDRO-1-METHYL-2-OXO-5-PHENYL-1H-1,4-BENZODIAZEPIN-3-YL)-TRICYCLO(3.3.1.1(3,7))DECANE-1-ACETAMIDE)

(+/−)-N-(2,3-DIHYDRO-1-METHYL-2-OXO-5-PHENYL-1H-1,4-BENZODIAZEPIN-3-YL)-N'-TRICYCLO(3.3.1.1(3,7))DEC-1-YL-METHYL)-UREA (+/−)-N-(2,3-DIHYDRO-1-METHYL-2-OXO-5-PHENYL-1H-1,4-BENZODIAZEPIN-3-YL)-3-METHYLTRICYCLO(3.3.1.1(3.7))DECANE-1-ACETAMIDE (1S)-(1.ALPHA.(RS),4.ALPHA.))-N-(2,3-DIHYDRO-1-METHYL-2-OXO-5-PHENYL-1H-1,4-BENZODIAZEPIN-3-YL)-7,7-DIMETHYL-2-OXO-BICYCLO(2.2.1)HEPTANE-1-METHANESULFONAMIDE (1R-(1.ALPHA.(RS),4.ALPHA.))-N-(2,3-DIHYDRO-1-METHYL-2-OXO-5-PHENYL-1H1,4-BENZODIAZEPIN-3-YL)-7,7-DIMETHYL-2-OXO-BICYCLO(2.2.1)HEPTANE-1-METHANESULFONAMIDE (+/−)-N-(2,3-DIHYDRO-1-METHYL-2-OXO-5-PHENYL-1H-1,4-BENZODIAZEPIN-3-YL)-N'-TRICYCLO(3.3.1.0(3,7))DEC-2-YL-UREA

ALPHA.-((((2,3-DIHYDRO-1-METHYL-2-OXO-5-PHENYL-1H-1,4-BENZODIAZEPIN-3-YL)AMINO)CARBONYL)AMINO)BENZENEACETIC ACID ETHYL ESTER, ALPHA ISOMER (+/−)-1,2,3,5-TETRAHYDRO-1-METHYL-2-OXO-5-PHENYL-N-(TRICYCLO(3.3.1.1.(3,7))DEC-1-

YLMETHYL)-4H-1,4-BENZODIAZEPINE-4-CARBOXAMIDE (+/−)-1,2,3,5-TETRAHYDRO-1-METHYL-2-OXO-5-PHENYL-N-TRICYCLO(3.3.1.1(3,7))DEC-2-YL-4H-1,4-BENZODIAZEPINE-4-CARBOXAMIDE (1R-(1.ALPHA.(R*),4.ALPHA.))-N-(2,3-DIHYDRO-1-METHYL-2-OXO-5-PHENYL-1H-1,4-BENZODIAZEPIN-3-YL)-7,7-DIMETHYL-2-OXOBICYCLO(2.2.1)HEPTANE-1-METHANESULFONAMIDE (1R-(1.ALPHA.(S*),4.ALPHA.))-N-(2,3-DIHYDRO-1-METHYL-2-OXO-5-PHENYL-1H-1,4-BENZODIAZEPIN-3-YL)-7,7-DIMETHYL-2-OXOBICYCLO(2.2.1)HEPTANE-1-METHANESULFONAMIDE

N-(2,3-DIHYDRO-1-METHYL-2-OXO-5-PHENYL-1H-1,4-BENZODIAZEPIN-3-YL)-2-HYDROXY-7,7-DIMETHYL-BICYCLO(2.2.1)HEPTANE-1-METHANESULFONAMIDE, ISOMER A AND ISOMER B

N-(2,3-DIHYDRO-1-METHYL-2-OXO-5-PHENYL-1H-1,4-BENZODIAZEPIN-3-YL)-2-HYDROXY-7,7-DIMETHYL-BICYCLO(2.2.1)HEPTANE-1-METHANESULFONAMIDE,

[3(S)-N-(2,3-DIHYDRO-1-METHYL-2-OXO-5-PHENYL-1H-1,4-BENZODIAZEPIN-3-YL)]-2-OXO-1,7,7-TRIMETHYL-BICYCLO(2.2.1)HEPTANE-3-ACETAMIDE

[3(R)-N-(2,3-DIHYDRO-1-METHYL-2-OXO-5-PHENYL-1H-1,4-BENZODIAZEPIN-3-YL)]-2-OXO-1,7,7-TRIMETHYL-BICYCLO(2.2.1)HEPTANE-3-ACETAMIDE (1S-(1.ALPHA.(S*),4.ALPHA.))-N-(2,3-DIHYDRO-1-METHYL-2-OXO-5-PHENYL-1H-1,4-BENZODIAZEPIN-3-YL)-7,7-DIMETHYL-2-OXOBICYCLO(2.2.1)HEPTANE-1-METHANESULFONAMIDE (1S-(1.ALPHA.(R*),4.ALPHA.))-N-(2,3-DIHYDRO-1-METHYL-2-OXO-5-PHENYL-1H-1,4-BENZODIAZEPIN-3-YL)-7,7-DIMETHYL-2-OXOBICYCLO(2.2.1)HEPTANE-1-METHANESULFONAMIDE

[3(S)-N-(2,3-DIHYDRO-1-METHYL-2-OXO-5-PHENYL-1H-1,4-BENZODIAZEPIN-3-YL)]-2-HYDROXY-1,7,7-TRIMETHYL-BICYCLO(2.2.1)HEPTANE-3-ACETAMIDE, ISOMER A AND ISOMER B

[3(R)-N-(2,3-DIHYDRO-1-METHYL-2-OXO-5-PHENYL-1H-1,4-BENZODIAZEPIN-3-YL)]-2-OXO-1,7,7-TRIMETHYLBICYCLO(2.2.1)HEPTANE-3-CARBOXAMIDE

4. A compound of claim 3 which is:

(+)-N-(2,3-DIHYDRO-1-METHYL-2-OXO-5-PHENYL-1H-1,4-BENZODIAZEPIN-3-YL)-N'-TRICYCLO(3.3.1.1(3,7))DEC-2-YL-UREA (R)-N-(2,3-DIHYDRO-1-METHYL-2-OXO-5-PHENYL-1H-1,4-BENZODIAZEPIN-3-YL)-N'-TRICYCLO(3.3.1.1(3,7))DEC-1-YL-UREA (1R-(1.ALPHA.(S*),4.ALPHA.))-N-(2,3-DIHYDRO-1-METHYL-2-OXO-5-PHENYL-1H-1,4-BENZODIAZEPIN-3-YL)-7,7-DIMETHYL-2-OXOBICYCLO(2.2.1)HEPTANE-1-METHANESULFONAMIDE

N-(2,3-DIHYDRO-1-METHYL-2-OXO-5-PHENYL-1H-1,4-BENZODIAZEPIN-3-YL)-2-HYDROXY-7,7-DIMETHYL-BICYCLO(2.2.1)HEPTANE-1-METHANESULFONAMIDE.

5. A pharmaceutical composition which comprises a pharmaceutically-acceptable carrier and an amount of the compound as claimed in claim 1 effective to prevent pre-term labor in a mammal in need thereof.

6. A pharmaceutical composition which comprises a pharmaceutically-acceptable carrier and an amount of the compound as claimed in claim 1 effective to treat dysmenorrhea in a mammal in need thereof.

7. A pharmaceutical composition which comprises a pharmaceutically acceptable carrier and an amount of the compound as claimed in claim 1 effective to stop labor preparatory to caesarean delivery.

* * * * *